United States Patent
Ohnuki et al.

(10) Patent No.: US 8,273,883 B2
(45) Date of Patent: Sep. 25, 2012

(54) METHOD FOR PRODUCING OPTICALLY ACTIVE 2-ARYLPIPERAZINE DERIVATIVE

(75) Inventors: Masatoshi Ohnuki, Takasago (JP);
Akira Nishiyama, Takasago (JP);
Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 462 days.

(21) Appl. No.: 12/449,460

(22) PCT Filed: Feb. 5, 2008

(86) PCT No.: PCT/JP2008/051856
§ 371 (c)(1),
(2), (4) Date: Aug. 10, 2009

(87) PCT Pub. No.: WO2008/099715
PCT Pub. Date: Aug. 21, 2008

(65) Prior Publication Data
US 2010/0087643 A1    Apr. 8, 2010

(30) Foreign Application Priority Data
Feb. 9, 2007  (JP) ................. 2007-030362

(51) Int. Cl.
C07D 241/04    (2006.01)
C07D 295/00    (2006.01)
(52) U.S. Cl. .................................... 544/395
(58) Field of Classification Search .............. 544/395
See application file for complete search history.

(56) References Cited

U.S. PATENT DOCUMENTS

| | | |
|---|---|---|
| 2004/0132736 A1 | 7/2004 | Guzi et al. |
| 2004/0157858 A1 | 8/2004 | Pentassuglia |
| 2006/0229300 A1 | 10/2006 | Wieringa et al. |
| 2006/0252768 A1 | 11/2006 | Watanabe et al. |

FOREIGN PATENT DOCUMENTS

| | | | |
|---|---|---|---|
| JP | 2006-521370 | | 9/2006 |
| WO | 02/081461 | | 10/2002 |
| WO | 03/022835 | | 3/2003 |
| WO | 2005/005410 | | 1/2005 |
| WO | WO 2006/060461 | * | 6/2006 |
| WO | WO 2007/057687 | * | 5/2007 |

OTHER PUBLICATIONS

International Search Report issued Mar. 4, 2008 in the International (PCT) Application of which the present application is the U.S. National Stage.
Blythin, D.J. et al., Synthesis and $NK_1/NK_2$ Binding Activities of a Series of Diacyl-Substituted 2-Arylpiperazines, Bioorganic & Medicinal Chemistry Letters, 2002, vol. 12, pp. 3161-3165.
Le Bihan, G. et al., Design and Synthesis of Imidazoline Derivatives Active on Glucose Homeostasis in a Rat Model of Type II Diabetes. 2. Syntheses and Biological Activities of 1,4-Dialkyl-, 1,4-Dibenzyl, and 1-Benzyl-4-alkyl-2-(4',5'-dihydro-1' H-imidazol-2'-yl)piperazines and Isosteric Analogues of Imidazoline, Journal of Medicinal Chemistry, May 6, 1999, vol. 42/No. 9, pp. 1587-1603.
Extended European Search Report issued Jul. 19, 2011 for the European application (No. 08 71 0788) corresponding to the present U.S. application.
Form PCT/IB/338 dated Aug. 20, 2009 and International Preliminary Report on Patentability including translation of PCT written opinion issued in International (PCT) Application of which the present application is the U.S. National Stage.
Wikstrom et al., "Synthesis and Pharmacological Testing of 1,2,3,4,10,14b-Hexahydro-6-methoxy-2-methyldibenzo [c,f] pyrazino [1,2-a] azepin and Its Enantiomers in Comparison with the Two Antidepressants Mianserin and Mirtazapine", J. Med. Chem. 2002, 45, pp. 3280-3285.
Rajeev et al., "Conformationally Restrained Chiral Analogues of Spermine: Chemical Synthesis and Improvements in DNA Triplex Stability", J. Org. Chem 1997, 62, pp. 5169-5173.
Bettoni et al., "Synthesis and Absolute Configuration of Substituted Morpholines", Tetrahedron vol. 36, pp. 409-415, 1980.
Kozlowski et al., "Substituted 2-(R)-Methyl Piperazines as Muscarinic M2 Selective Ligands", Bioorganic & Medicinal Chemistry Letters 12, 2002, pp. 791-794.

* cited by examiner

Primary Examiner — Erich A Leeser
(74) Attorney, Agent, or Firm — Wenderoth, Linds & Ponack, L.L.P.

(57) ABSTRACT

The objective of the present invention is to produce an optically active 2-arylpiperazine derivative useful as a synthetic intermediate for pharmaceutical products and agricultural chemicals from inexpensive and readily available starting material by an industrially practicable method. The objective can be accomplished by treating an optically active substituted aminodiol derivative produced from an optically active styrene oxide derivative with a sulfonating agent in the presence of a base, and then reacting an amine compound to obtain the 2-arylpiperazine derivative. Especially, an optically active 1-unsubstituted-2-arylpiperazine derivative can be produced by treating an optically active 1-allyl-2-arylpiperazine derivative with water in the presence of a transition metal catalyst for deallylation.

11 Claims, No Drawings

METHOD FOR PRODUCING OPTICALLY ACTIVE 2-ARYLPIPERAZINE DERIVATIVE

TECHNICAL FIELD

The present invention relates to a method for producing an optically active 2-arylpiperazine derivative, which is useful as a synthetic intermediate for pharmaceutical products and agricultural chemicals.

BACKGROUND ART

There are following methods for producing an optically active 2-arylpiperazine derivative:
(1) a method, wherein 4-chlorophenacyl bromide is asymmetrically reduced, converted into the corresponding epoxy derivative, aminated, converted into the corresponding thiazolidine compound, azidated, reduced, cyclizated and reduced to produce the corresponding (R)-4-benzyl-2-(4-chlorophenyl)-piperazine (Patent Document 1);
(2) a method for producing (S)-2-(5-fluorotoluen-2-yl)piperazine, wherein the coupling reaction of 2-bromo-5-fluorotoluene with a ketocarboxylic acid derivative is carried out, the product is cyclized using ethylene diamine, hydrogenated and reduced to yield racemate of 2-(5-fluorotoluen-2-yl)piperazine, and the enantiomers of the racemic substance is separated (Patent Document 2);
(3) a method, wherein optically active (S)—N-(tert-butoxycarbonyl)phenylglycine and a glycine derivative are subjected to dehydration condensation to yield an amide derivative, and the amide derivative is cyclized and reduced to produce the corresponding (S)-4-benzyl-2-phenylpiperazine (Patent Document 3).

Patent Document 1: JP 2006-521370 A
Patent Document 2: WO 2002/081461
Patent Document 3: WO 2003/022835

DISCLOSURE OF THE INVENTION

Problems to be Solved by the Invention

However, the conventional art (1) cannot be regarded to be industrially preferable, since the conventional art requires many steps, and an expensive asymmetrically reducing agent is used in a stoichiometric amount, and the process proceeds via a step of producing an azide intermediate with high risk of explosion. The conventional art (2) is problematic in that an expensive ketocarboxylic acid derivative and reducing agent are used, and the productivity is lowered due to finally conducted optical resolution. The conventional art (3) is problematic in use of an expensive condensing agent and reducing agent, and cannot be regarded as a highly versatile production method since an unnatural amino acid is necessary as the starting material depending on substituent on the aryl group.

Means for Solving the Problems

The present inventors made extensive study in view of the circumstances described above; and as a result, the inventors found that an optically active 2-arylpiperazine derivative can be easily produced with high yield by treating an optically active substituted aminodiol derivative produced from an optically active styrene oxide derivative with a sulfonylating agent in the presence of a base, and then reacting the product with an amine compound. The inventors particularly found that deallylation of an optically active 1-allyl-2-arylpiperazine derivative can advance by allowing water to further act thereon in the presence of a transition metal catalyst, to produce the corresponding optically active 1-unsubstituted-2-arylpiperazine derivative; and the present invention was thereby completed.

The present invention relates to a method for producing an optically active 2-arylpiperazine derivative or salt thereof, comprising steps of:
treating an optically active substituted aminodiol derivative represented by the following formula (4):

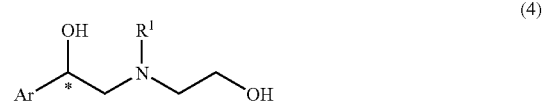

(4)

wherein, Ar represents an optionally substituted aryl group having 6 to 20 carbon atoms, or an optionally substituted heteroaryl group having 3 to 20 carbon atoms; $R^1$ represents an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; * indicates an asymmetric carbon atom,
with a sulfonating agent in the presence of a base;
and then reacting an amine compound represented by the following formula (5):

$R^2NH_2$ (5)

wherein, $R^2$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms;
wherein, the optically active 2-arylpiperazine derivative is represented by the following formula (1):

(1)

wherein, Ar, $R^1$, $R^2$, * mean the same as the above.

Further, the present invention relates to a method for producing an optically active 1-unsubstituted-2-arylpiperazine derivative or salt thereof, comprising a step of:
treating an optically active 1-allyl-2-arylpiperazine derivative represented by the following formula (2):

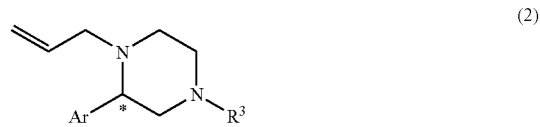

(2)

wherein, Ar represents an optionally substituted aryl group having 6 to 20 carbon atoms, or an optionally substituted heteroaryl group having 3 to 20 carbon atoms; $R^3$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, an optionally substituted heteroaryl group having 3 to 20 carbon atoms, or a protecting group for the amino group; * indicates an asymmetric carbon atom,
or salt thereof with water in the presence of a transition metal catalyst,
wherein the optically active 1-unsubstituted-2-arylpiperazine derivative is represented by the following formula (3):

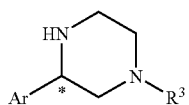

(3)

wherein, Ar, $R^3$, * mean the same as the above.

Furthermore, the present invention relates to an optically active 1-allyl-2-arylpiperazine derivative represented by the following formula (2):

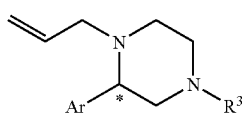

(2)

wherein, Ar represents an optionally substituted aryl group having 6 to 20 carbon atoms, or an optionally substituted heteroaryl group having 3 to 20 carbon atoms; $R^3$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, an optionally substituted heteroaryl group having 3 to 20 carbon atoms, or a protecting group for the amino group; * indicates an asymmetric carbon atom,
or salt thereof.

EFFECT OF THE INVENTION

According to the present invention, a high-quality optically active 2-arylpiperazine derivative can be produced easily and efficiently from inexpensive and readily available starting material by an industrially practicable method.

BEST MODE FOR CARRYING OUT THE INVENTION

First, the starting material used in the present invention and the products are described.

The optically active styrene oxide derivative used as a starting material for the optically active aminodiol derivative and the optically active substituted aminodiol derivative in the present invention is represented by the following formula (6):

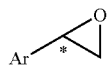

(6)

wherein, Ar represents an optionally substituted aryl group having 6 to 20 carbon atoms or an optionally substituted heteroaryl group having 3 to 20 carbon atoms. Examples of the aryl group include a phenyl group, a naphthyl group, a biphenyl group and the like. Examples of the heteroaryl group include a pyridyl group, a furanyl group, a thienyl group, a pyrrolyl group, an oxazolyl group, an isooxazolyl group, a pyrazolyl group, a benzofuranyl group, a benzothiazolyl group, an indolyl group and the like.

The substituent can be exemplified by a halogen atom such as a fluorine atom, a chlorine atom, a bromine atom or an iodine atom, a nitro group, a nitroso group, a cyano group, an amino group, a hydroxyamino group, an alkylamino group having 1 to 12 carbon atoms, a dialkylamino group having 1 to 12 carbon atoms, an aralkylamino group having 7 to 12 carbon atoms, a diaralkylamino group having 7 to 12 carbon atoms, an alkylsulfonylamino group having 1 to 12 carbon atoms, a sulfonic acid group, a sulfonamide group, an azide group, a trifluoromethyl group, a carboxyl group, an acyl group having 1 to 12 carbon atoms, an aroyl group having 7 to 12 carbon atoms, a hydroxyl group, an alkyloxy group having 1 to 12 carbon atoms, an aralkyloxy group having 7 to 12 carbon atoms, an aryloxy group having 6 to 12 carbon atoms, an acyloxy group having 1 to 12 carbon atoms, an aroyloxy group having 7 to 12 carbon atoms, a silyloxy group having 3 to 12 carbon atoms, an alkylsulfonyloxy group having 1 to 12 carbon atoms, an alkylthio group having 1 to 12 carbon atoms and the like. The number of the substituents may be 0 to 5.

A phenyl group or a 4-chlorophenyl group is particularly preferable as Ar.

The denotation, "*", indicates an asymmetric carbon atom. All of the mixture of enantiomers including even a slight amount of one enantiomer in excess is involved in the scope of the present invention.

The method for obtaining the compound (6) is not particularly limited, and a method described in JP 2006-521370 A or the like is specifically exemplified.

The aminoethanol derivative used as the starting material for the optically active substituted aminodiol derivative in the present invention is represented by the following formula (7):

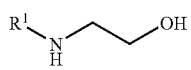

(7)

wherein, $R^1$ represents an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms.

Examples of the alkyl group include a methyl group, an ethyl group, an n-propyl group, an isopropyl group, an n-butyl group, a tert-butyl group and the like. Examples of the cycloalkyl group include a cyclopropyl group, a cyclopentyl group, a cyclohexyl group and the like. Examples of the alkenyl group include a vinyl group, an allyl group, a methallyl group and the like. Examples of the aralkyl group include a benzyl group, a 1-phenethyl group and the like. Examples of the aryl group include a phenyl group, a naphthyl group, a biphenyl group and the like. Examples of the heteroaryl group include a pyridyl group, a furanyl group, a thienyl group, a pyrrolyl group, an oxazolyl group, an isooxazolyl group, a pyrazolyl group, a benzofuranyl group, a benzothiazolyl group, an indolyl group and the like. Examples of the substituent and the number thereof are the same as the above definition of Ar.

$R^1$ is preferably an alkyl group such as a methyl group, an ethyl group, an n-propyl group, an isopropyl group, an n-butyl group or a tert-butyl group; an alkenyl group such as a vinyl group, an allyl group or a methallyl group; an aralkyl group such as a benzyl group or a 1-phenethyl group; or an aryl group such as a phenyl group, a naphthyl group or a biphenyl group; and more preferably a methyl group, an allyl group, a phenyl group or a benzyl group.

The optically active substituted aminodiol derivative used in the present invention is obtained by reacting the optically active styrene oxide derivative with the aminoethanol derivative, and is represented by the following formula (4):

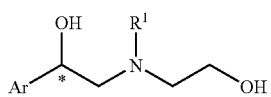

(4)

wherein Ar, $R^1$ and * are the same as defined above.

The optically active aminodiol derivative used in the present invention is obtained by reacting the optically active styrene oxide derivative with aminoethanol, and is represented by the following formula (4'):

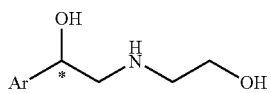

(4')

wherein Ar and * are the same as defined above.

The amine compound used in the present invention is represented by the following formula (5):

$R^2NH_2$ (5)

wherein, $R^2$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms.

The Specific examples of the groups are the same as the examples in the above definition of $R^1$. Examples of the substituent that the above groups may have and the number of the substituents are also the same as the above definition of $R^1$.

$R^2$ is preferably a hydrogen atom; an alkyl group such as a methyl group, an ethyl group, an n-propyl group, an isopropyl group, an n-butyl group or a tert-butyl group; an alkenyl group such as a vinyl group, an allyl group or a methallyl group; an aralkyl group such as a benzyl group or a 1-phenethyl group; or an aryl group such as a phenyl group, a naphthyl group or a biphenyl group; and more preferably a hydrogen atom, a methyl group, a tert-butyl group or an allyl group.

The optically active 2-arylpiperazine derivative in the present invention and salt thereof can be obtained from the optically active substituted aminodiol derivative, and are represented by the following formula (1):

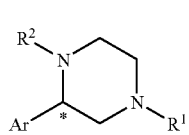

(1)

wherein, Ar, $R^1$, $R^2$ and * are the same as defined above.

The optically active 1-allyl-2-arylpiperazine derivative in the present invention and salt thereof can be obtained from the optically active substituted aminodiol derivative, and is represented by the following formula (2):

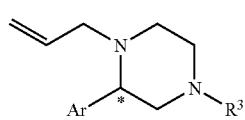

(2)

wherein, Ar and * are the same as defined above; and $R^3$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, an optionally substituted heteroaryl group having 3 to 20 carbon atoms, or a protecting group for the amino group.

The specific examples of the alkyl group, cycloalkyl group, alkenyl group, aryl group and heteroaryl group are the same as the examples in the definition of $R^1$. Examples of the protecting group for the amino group include protecting groups for secondary amine described in JOHN WILEY & SONS, INC., "PROTECTIVE GROUPS in ORGANIC SYNTHESIS", Third edition, written by Theodora W. Greene, pp. 494-653.

Examples of the substituent that the above groups may have and the number of the substituent are also the same as the examples in the definition of $R^1$.

$R^3$ is preferably a hydrogen atom; an alkyl group such as a methyl group, an ethyl group, an n-propyl group, an isopropyl group, an n-butyl group or a tert-butyl group; an alkenyl group such as a vinyl group, an allyl group or a methallyl group; an aralkyl group such as a benzyl group or a 1-phenethyl group; an aryl group such as a phenyl group, a naphthyl group or a biphenyl group; a carbamate protecting group such as a methoxycarbonyl group, an ethoxycarbonyl group or a benzyloxycarbonyl group; and more preferably a hydrogen atom, a methyl group, an allyl group, a benzyl group, a phenyl group or an ethoxycarbonyl group.

The optically active 1-allyl-2-arylpiperazine derivative and salt thereof are novel compounds and not described in any literatures.

The optically active 1-unsubstituted-2-arylpiperazine derivative in the present invention and salt thereof can be obtained from the 1-allyl-2-arylpiperazine derivative or the optically active substituted aminodiol derivative, and are represented by the following formula (3):

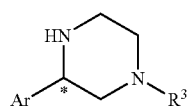

wherein, Ar, $R^3$ and * are the same as defined above.

Hereinafter, the method for producing the optically active substituted aminodiol derivative, optically active 2-arylpiperazine derivative and the like is described.

The present invention can be schematically shown as below, and the respective steps are described in order.

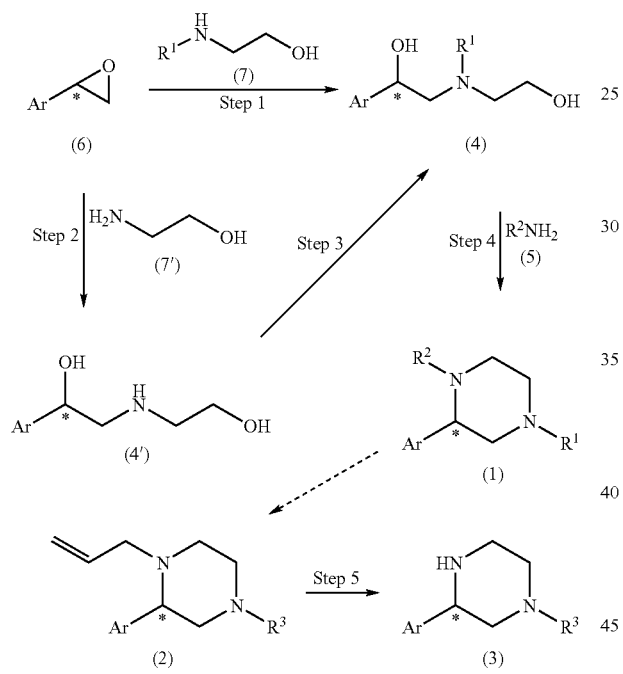

Step 1

In the step, the optically active styrene oxide derivative represented by the formula (6) is reacted with the aminoethanol derivative represented by the formula (7), to produce the optically active substituted aminodiol derivative represented by the formula (4).

The reaction in the step does not particularly require a reaction solvent, but a reaction solvent may be added in such a case where stirring is difficult due to a low solubility of the substrate.

The reaction solvent is not particularly limited as long as the solvent does not influence the reaction; and examples thereof include water; alcohol solvents such as methanol, ethanol, n-propanol, isopropanol, n-butanol, tert-butanol and ethylene glycol; ether solvents such as tetrahydrofuran, diethyl ether, 1,4-dioxane and ethylene glycol dimethyl ether; aromatic hydrocarbon solvents such as benzene and toluene; aliphatic hydrocarbon solvents such as pentane, hexane, heptane and methylcyclohexane; halogen solvents such as carbon tetrachloride, chloroform, methylene chloride, 1,2-dichloroethane and chlorobenzene; ester solvents such as ethyl acetate, isopropyl acetate and tert-butyl acetate; sulfoxide solvents such as dimethylsulfoxide; amide solvents such as N,N-dimethylformamide and N,N-dimethylacetamide; urea solvents such as dimethyl propyleneurea; phosphonic triamide solvents such as hexamethylphosphonictriamide; ketone solvents such as acetone and methyl ethyl ketone; and nitrile solvents such as acetonitrile and propionitrile.

The solvent is preferably water; aromatic hydrocarbon solvents such as benzene or toluene; ether solvents such as tetrahydrofuran, 1,4-dioxane or methyl tert-butyl ether; or ester solvents such as ethyl acetate, isopropyl acetate or tert-butyl acetate; and more preferably water, tetrahydrofuran or toluene. The only one solvent may be used, or the mixture of the two or more solvents may be used. When the two or more solvents are used in combination, the mixing ratio is not particularly limited.

The amount of the solvent to be used is preferably not higher than 50 times by weight, and more preferably not higher than 20 times by weight, relative to the weight of the compound (6), since too large amount of the solvent is disadvantageous to costs and post-treatment.

The amount of the compound (7) to be used is preferably 0.5 to 10 times by mole, more preferably 0.5 to 5 times by mole, and even more preferably 0.5 to 3 times by mole, relative to the mole of the compound (6), from the viewpoints of reaction yield improvement and economic efficiency.

The reaction temperature in the step is preferably 0 to 150° C., and more preferably 20 to 100° C., for the purpose of reducing the reaction time while side reactions are suppressed.

The reaction time in the step is not particularly limited and may be arbitrarily decided. The reaction time is preferably 1 to 24 hours, and more preferably 3 to 12 hours.

In the reaction, the addition method and addition order of the compound (6), the compound (7) and a reaction solvent are not particularly limited.

After the reaction is completed, the compound (4) may be used directly in the subsequent step without isolation. In the step, however, the compound (4) is contaminated with regioisomer thereof as a byproduct. The regioisomer is represented by the following formula (8):

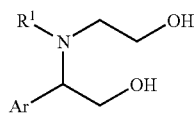

wherein, Ar and $R^1$ are the same as defined above. For the purpose of removing the impurity, general purification such as crystallization, fractional distillation, column chromatography or the like may be carried out. Preferably, the compound (4) may be reacted with an acid to form a salt and then the salt is precipitated as a crystal from the solvent, whereby the salt is separated as crystals while the regioisomer (8) is removed in the mother liquid.

Examples of the acid used for forming the salt include inorganic acids such as hydrogen fluoride, hydrogen chloride, hydrogen bromide, hydrogen iodide, sulfuric acid, nitric acid, phosphoric acid and boric acid; carboxylic acids such as formic acid, acetic acid, propionic acid, butyric acid, pivalic acid, chloroacetic acid, trichioroacetic acid, trifluoroacetic acid, oxalic acid, L-tartaric acid, D-tartaric acid and mandelic acid; and sulfonic acids such as methanesulfonic acid, trifluoromethanesulfonic acid, benzenesulfonic acid, p-toluenesulfonic acid and camphorsulfonic acid. The acid is preferably hydrogen chloride, hydrogen bromide, sulfuric acid, acetic acid, pivalic acid, oxalic acid, L-tartaric acid, D-tartaric acid, mandelic acid, methanesulfonic acid, p-toluenesulfonic acid or camphorsulfonic acid, and more preferably hydrogen chloride.

The amount of the acid to be used is preferably 0.5 to 5 times by mole, and more preferably 0.5 to 1.5 times by mole, relative to the mole of the compound (4).

The solvent is not limited; and examples thereof include water; alcohol solvents such as methanol, ethanol, n-propanol, isopropanol, n-butanol, tert-butanol and ethylene glycol; ether solvents such as tetrahydrofuran, diethyl ether, 1,4-dioxane and ethylene glycol dimethyl ether; aromatic hydrocarbon solvents such as benzene and toluene; aliphatic hydrocarbon solvents such as pentane, hexane, heptane and methylcyclohexane; halogen solvents such as carbon tetrachloride, chloroform, methylene chloride, 1,2-dichloroethane and chlorobenzene; ester solvents such as ethyl acetate, isopropyl acetate and tert-butyl acetate; sulfoxide solvents such as dimethylsulfoxide; amide solvents such as N,N-dimethylformamide and N,N-dimethylacetamide; urea solvents such as dimethyl propyleneurea; phosphonic triamide solvents such as hexamethylphosphonic triamide; ketone solvents such as acetone and methyl ethyl ketone; and nitrile solvents such as acetonitrile and propionitrile.

The solvent is preferably alcohol solvents such as methanol, ethanol, n-propanol, isopropanol, n-butanol, tert-butanol or ethylene glycol; aromatic hydrocarbon solvents such as benzene or toluene; ketone solvents such as acetone or methyl ethyl ketone; or ester solvents such as ethyl acetate, isopropyl acetate or tert-butyl acetate; and more preferably isopropanol, acetone, ethyl acetate or toluene. The only one solvent may be used, or the mixture of the two or more solvents may be used. When the two or more solvents are used in combination, the mixing ratio is not particularly limited.

The amount of the solvent to be used is preferably not higher than 50 times by weight, and more preferably not higher than 20 times by weight, relative to the weight of the compound (4), since too large amount of the solvent is disadvantageous to costs and post-treatment.

The process for crystallization is not limited, and examples thereof include the following processes:
(a) a process for crystallization by mixing the compound (4) with an aqueous solution of the acid or with the acid and water in an organic solvent, and then concentrating the mixture and removing water by distillation. In the case, an organic solvent azeotropic with water, such as ethyl acetate and toluene, may be used to distill water away by azeotropic effect;
(b) a process for crystallization by mixing the compound (4) with the acid in an organic solvent;
(c) a process for crystallization by mixing the compound (4) with the acid in an organic solvent and cooling the mixture.

The above processes for crystallization may be appropriately selected depending on the kind of the acid and the combination with the organic solvent. For example, when hydrogen chloride or hydrogen bromide is used, an aqueous solution thereof, that is, hydrochloric acid or hydrobromic acid, can be more easily treated; and therefore, the process (a) is more suitable. When an acid such as methanesulfonic acid or acetic acid that can be generally easily usable as a nonhydrate is used, the process (b) is preferably selected.

The salt obtained by the process (a), (b) or (c) may be further subjected to with any of the following crystallization processes (d) and (e) in combination:
(d) a process for crystallization by dissolving the salt of the compound (4) in an organic solvent and then cooling the solution;
(e) a process for crystallization by dissolving the salt of the compound (4) in an organic solvent and then adding a poor solvent to the solution, or concentrating the solution and substituting the solvent with a poor solvent.

Examples of the poor solvent used in the process (e) include toluene, hexane and the like. The processes (a), (b), (c), (d) and (e) may be appropriately combined for crystallization. For crystallization, seed crystals may be added.

The temperature in the crystallization processes (a) to (e) is not particularly limited, and may be selected appropriately depending on the kind of the salt and the kind of the solvent to be used, and may be preferably decided depending on the desired amount of precipitated crystals and the desired quality of the crystals within lower than the temperature at which the salt of the compound (4) is dissolved in the solvent or the mixed solvent to be used.

The salt of the compound (4) precipitated in the crystallization processes (a) to (e) can be separated and obtained by a procedure such as vacuum filtration, pressure filtration or centrifugation. When the purity of the crystals is lowered due to the remaining mother liquid in the crystals, the quality can be improved by further washing the crystals with an organic solvent if necessary.

Drying under reduced pressure or under vacuum at about 60° C. or less is preferable as a method for drying the crystals, so as to avoid thermal decomposition and melting.

The salt of the compound (4) obtained by the above processes may further be treated with a base such as an alkali metal hydroxide to liberate the compound (4), and an operation such as extraction and concentration may be carried out, to obtain the compound (4) with improved chemical purity.

Step 2

In the step, the optically active styrene oxide derivative represented by the formula (6) is reacted with the aminoethanol (7') represented by the formula (7) wherein $R^1$ is a hydrogen atom, to produce the optically active aminodiol derivative represented by the formula (4').

In the step, the reaction solvent, the amounts of the reagents to be used, the reaction temperature, the reaction time, the order of adding the reagents, and the treatment after the reaction are the same as those described in step 1.

Step 3

In the step, the optically active substituted aminodiol derivative represented by the formula (4) is produced by introducing a substituent into the amino group of the optically active aminodiol derivative which is represented by the formula (4') and produced in step 2.

In the step, the method for introducing $R^1$ varies depending on the kind of $R^1$, and the most appropriate method may be selected. For example, when $R^1$ is an optionally substituted alkyl group having 1 to 20 carbon atoms, an optionally substituted cycloalkyl group having 3 to 20 carbon atoms, an optionally substituted alkenyl group having 2 to 20 carbon atoms, or an optionally substituted aralkyl group having 7 to 20 carbon atoms, the compound (4') may be reacted with the corresponding organic halide compound, organic sulfonate compound, organic phosphate compound or the like in the presence of a base.

When $R^1$ is an optionally substituted aryl group having 6 to 20 carbon atoms or an optionally substituted heteroaryl group having 3 to 20 carbon atoms, the compound (4') may be reacted with the corresponding aryl fluoride or heteroaryl fluoride, or be reacted with the corresponding aryl chloride, aryl bromide, aryl iodide, heteroaryl chloride, heteroaryl bromide or heteroaryl iodide in the presence of a palladium catalyst.

Specifically, when $R^1$ is an allyl group, the compound (4') may be reacted with an allyl halide such as allyl chloride, allyl bromide or allyl iodide in the presence of a base.

Examples of the base include tertiary amines such as triethylamine, tri-n-butylamine, N-methylmorpholine, N-methylpiperidine, diisopropylethylamine, pyridine, N,N-dimethylaminopyridine and 1,4-diazabicyclo[2,2,2]octane; metal hydroxides such as lithium hydroxide, sodium hydroxide, potassium hydroxide, barium hydroxide and magnesium hydroxide; metal carbonates such as lithium carbonate, sodium carbonate and potassium carbonate; and metal hydrogencarbonates such as lithium hydrogencarbonate, sodium hydrogencarbonate and potassium hydrogencarbonate. The base is preferably tertiary amines such as triethylamine, tri-n-butylamine, N-methylmorpholine, N-methylpiperidine, diisopropylethylamine, pyridine, N,N-dimethylaminopyridine or 1,4-diazabicyclo[2,2,2]octane, and more preferably triethylamine.

The amount of the base to be used is preferably 0.1 to 10 times by mole, and more preferably 1 to 5 times by mole, relative to the mole of the compound (4').

The amount of the allyl halide to be used is preferably 1 to 10 times by mole, and more preferably 1 to 5 times by mole, relative to the mole of the compound (4').

The reaction temperature in the step is preferably −20° C. to 80° C., and more preferably 0° C. to 50° C., for the purpose of reducing the reaction time while side reactions are suppressed.

The reaction time in the step is not particularly limited; but is preferably 1 to 24 hours, and more preferably 3 to 12 hours. In the reaction, the addition method and addition order of the compound (4'), the base, the allyl halide and the solvent are not particularly limited.

General treatment for obtaining product from reaction mixture may be carried out as a post-treatment of the reaction. For example, water is added to the reaction mixture after the reaction, or an aqueous solution of acid, such as hydrochloric acid or an aqueous solution of sulfuric acid, is added for neutralization if necessary; and then, extraction is carried out with a general extraction solvent such as ethyl acetate, diethyl ether, methylene chloride, toluene or hexane. The extract thus obtained is subjected to procedures such as heating under reduced pressure for distilling off the reaction solvent and the extraction solvent, to give the desired substance. The desired substance thus obtained has purity sufficient for use in the subsequent step; but the purity may further be improved by general purification method such as crystallization, fractional distillation and column chromatography in order to further increase the yield in the subsequent step or to further increase the purity of the compound obtained in the subsequent step. As described in step 1, the purity of the product may be increased by forming the salt thereof with an acid and precipitating the salt as crystals from the solvent.

Step 4

In the step, the optically active substituted aminodiol derivative which is represented by the formula (4) and produced in step 1 or 3 is treated with a sulfonylating agent in the presence of a base, and then reacted with the amine compound represented by the formula (5), to produce the optically active 2-arylpiperazine derivative represented by the formula (1) or salt thereof.

As to the stereochemistry in the step, the configuration of the asymmetric carbon at 2-position to which the aryl group is bound is maintained. In other words, when the absolute configuration of the compound (4) is S, the absolute configuration of the compound (1) as the product becomes S; and when the absolute configuration of the compound (4) is R, the absolute configuration of the compound (1) as the product becomes R.

Although such kind of the reaction must proceed usually with stereochemical inversion, the stereochemistry is maintained in the step. The reason therefor is not well revealed; but it can be explained that the stereochemistry is inverted twice, that is, the product of which stereochemistry is maintained can be obtained, if it is assumed that the product is possibly synthesized via an aziridinium salt shown in the following scheme.

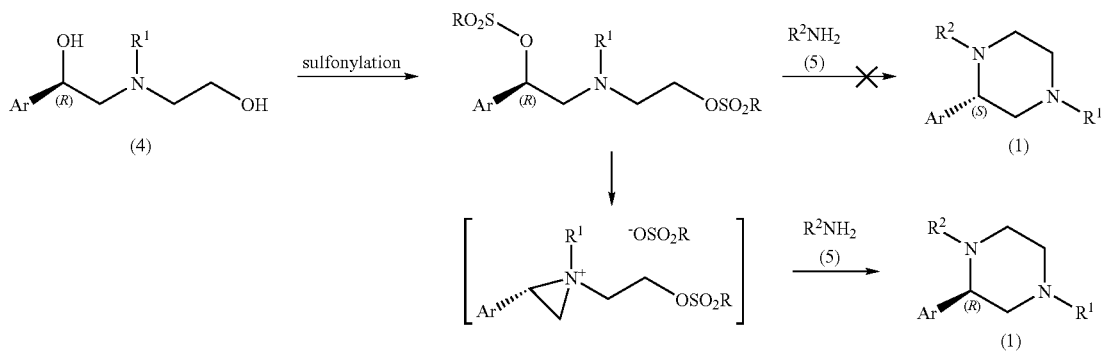

Preferable examples of the sulfonylating agent in the step include methanesulfonyl chloride, ethanesulfonyl chloride, trifluoromethanesulfonic anhydride, benzenesulfonyl chloride, 4-methylbenzenesulfonyl chloride, 4-chlorobenzenesulfonyl chloride, 2-nitrobenzenesulfonyl chloride, 3-nitrobenzenesulfonyl chloride and 4-nitrobenzenesulfonyl chloride; and methanesulfonyl chloride is particularly preferred.

The amount of the sulfonylating agent to be used is preferably 2 to 10 times by mole, and more preferably 2 to 5 times by mole, relative to the mole of the compound (4).

Examples of the base used in the sulfonylation in the step include the bases exemplified in the above step 3. The base is a preferably tertiary amines such as triethylamine, tri-n-butylamine, N-methylmorpholine, N-methylpiperidine, diisopropylethylamine, pyridine, N,N-dimethylaminopyridine or 1,4-diazabicyclo[2,2,2]octane, and more preferably triethylamine.

The amount of the base to be used is preferably 2 to 20 times by mole, and more preferably 2 to 10 times by mole, related to the mole of the compound (4).

As to the reaction solvent in the step, the base described above may be used. However, when the base is added only by the minimum amount from the viewpoint of economical efficiency, a reaction solvent may further be added from the purpose of securing fluidity.

Examples of the reaction solvent include ether solvents, aromatic hydrocarbon solvents, aliphatic hydrocarbon solvents, halogen solvents, ester solvents, sulfoxide solvents, amide solvents, urea solvents, phosphonic triamide solvents, ketone solvents and nitrile solvents. Specific examples thereof include the solvents exemplified as the reaction solvent in step 1.

The solvent is preferably ether solvents such as tetrahydrofuran, diethyl ether, 1,4-dioxane and ethylene glycol dimethyl ether; aromatic hydrocarbon solvents such as benzene and toluene; or ester solvents such as ethyl acetate, isopropyl acetate and tert-butyl acetate; and more preferably toluene or ethyl acetate. The only one solvent may be used, or the mixture of the two or more solvents may be used. When the two or more solvents are used in combination, the mixing ratio is not particularly limited.

The amount of the solvent to be used is preferably not higher than 50 times by weight, and more preferably not higher than 20 times by weight, relative to the weight of the compound (4), since too large amount of the solvent is disadvantageous to costs and post-treatment.

The reaction temperature for sulfonylation in the step is preferably −40° C. to 80° C., and more preferably −20° C. to 50° C., for the purpose of reducing the reaction time while side reactions are suppressed. The reaction time for sulfonylation in the step is not particularly limited and is preferably 0.1 to 24 hours, and more preferably 0.5 to 12 hours.

In the sulfonylation in the step, the addition method and addition order of the compound (4), the base, the sulfonylating agent and the reaction solvent are not particularly limited.

In the step, after sulfonylation is finished, the amine compound represented by the formula (5) is added to the reaction mixture to carry out cyclization reaction. When the compound (5) is in a liquid or solid form at ordinary temperatures, the compound (5) may be directly added; but when the compound (5) is in a gaseous form at ordinary temperatures, such as ammonia, methylamine or ethylamine, the compound (5) may be blown directly in a gaseous form into the reaction mixture or may be used as a solution dissolved in a solvent such as water, methanol, ethanol, isopropanol, 1,4-dioxane or tetrahydrofuran.

The amount of the compound (5) to be used is preferably 1 to 100 times by mole, and more preferably 1 to 20 times by mole, relative to the mole of the compound (4).

The reaction temperature for cyclization in the step is preferably −40° C. to 80° C., and more preferably −20° C. to 50° C., from the viewpoint of suppressing the formation of by-products.

The cyclization reaction time in the step is not particularly limited, and is preferably 1 to 24 hours, and more preferably 3 to 12 hours.

General treatment for obtaining product from reaction mixture may be carried out as a post-treatment of the reaction. For example, water is added to the reaction mixture after the reaction, or an aqueous solution of acid, such as hydrochloric acid or an aqueous solution of sulfuric acid, is added for neutralization if necessary; and then, extraction is carried out with a general extraction solvent such as ethyl acetate, diethyl ether, methylene chloride, toluene or hexane. The extract thus obtained is subjected to procedures such as heating under reduced pressure for distilling off the reaction solvent and the extraction solvent, to give the desired substance.

The desired substance thus obtained has purity sufficient for use in the subsequent step; but the purity may further be improved by general purification method such as crystallization, fractional distillation and column chromatography in order to further increase the yield in the subsequent step or to further increase the purity of the compound obtained in the subsequent step.

The chemical purity or optical purity of the compound (1) may be improved by forming salt thereof with an acid and subsequent precipitation from the solvent.

Examples of the acid used in forming the salt are the same as the acids exemplified for forming the salt of the compound (4) in step 1.

The amount of the acid to be used is preferably 0.5 to 10 times by mole, and more preferably 0.5 to 3 times by mole, relative to the mole of the compound (1).

The solvent used in crystallization is not particularly limited and can be the same as the solvents exemplified for crystallization of the salt between the compound (4) and an acid in step 1.

The amount of the solvent to be used is preferably not higher than 50 times by weight, and more preferably not higher than 20 times by weight, relative to the weight of the compound (1), since too large amount of the solvent is disadvantageous to costs and post-treatment.

The method for crystallization is not particularly limited, and the processes (a) to (e) described above as the method for crystallization of the compound (4) in step 1 may also be used. The method suitable for the combination of the acid and the solvent is also the same as described for the compound (4). Further, seed crystals may be added in crystallization.

The temperature in the crystallization processes (a) to (e) is not particularly limited, and may be selected appropriately depending on the kind of the salt and the kind of the solvent to be used, and may be preferably decided depending on the desired amount of the precipitated crystals and the desired quality of the crystals within lower than the temperature at which the salt of the compound (1) is dissolved in the solvent or the mixed solvent to be used.

The salt of the compound (1) precipitated in the crystallization processes (a) to (e) can be separated and obtained by a procedure such as vacuum filtration, pressure filtration or centrifugation. When the purity of the crystals is lowered due to the remaining mother liquid in the crystals, the quality can be improved by further washing the crystals with an organic solvent if necessary.

Drying under reduced pressure or under vacuum at about 60° C. or less, so as to avoid thermal decomposition and melting, is preferable as a method for drying the crystals.

The salt of the compound (1) obtained by the above processes may further be treated with a base such as an alkali metal hydroxide to liberate the compound (1), and an operation such as extraction and concentration may be carried out, to obtain the compound (1) with improved chemical purity or optical purity.

Step 5

In the step, the optically active 1-unsubstituted-2-aryl piperazine derivative represented by the formula (3) or salt thereof is produced by treating the optically active 1-allyl-2-aryl piperazine derivative represented by the formula (2) or salt thereof in the presence of a transition metal catalyst. In the step, the compound (3) can be efficiently obtained.

The compound (2) used in the step is preferably the product obtained by using allylamine in step 4. In such a case, $R^3$ in the compound (2) is the same as $R^1$ described above. The compound (2) in which $R^3$ is a protective group for the amino group, such as a carbamate group or an acyl group, can be easily produced by reacting the compound (2) in which $R^3$ is a benzyl group with a halocarbonate such as methyl chlorocarbonate, ethyl chlorocarbonate, n-propyl chlorocarbonate or isopropyl chlorocarbonate, or with an acyl halide such as acetyl chloride, pivaloyl chloride, benzoyl chloride or 4-methylbenzoyl chloride, so as to advance the substitution reaction of the benzyl group therewith.

In the step, when the compound (2) in which $R^3$ is an ally group is used as the starting material, deallylation proceeds simultaneously to give the compound (3) in which $R^3$ is a hydrogen atom.

The deallylation in the step is achieved by isomerizing a double bond of the allyl group by the action of the transition metal catalyst to form an enamine and by hydrolysis thereof. Although isomerization of the double bond and hydrolysis may be carried out in two stages, the isomerization of the double bond may be carried out in water so that the hydrolysis can simultaneously proceed from the viewpoint of simplifying the process.

Examples of the transition metal catalyst include transition metals of Group 8, such as iron, ruthenium and osmium; Group 9, such as cobalt, rhodium and iridium; and Group 10, such as nickel, palladium and platinum. Specific examples thereof include ruthenium in Group 8, rhodium in Group 9, palladium in Group 10 and platinum in Group 10.

More specific examples thereof include "ruthenium" such as carbon-supported ruthenium, ruthenium(III) chloride, ruthenium dioxide, dichlorotris(triphenylphosphine)ruthenium(II), chlorohydridotris(triphenylphosphine)ruthenium(II), acetatohydridotris(triphenylphosphine)ruthenium(II), carbonylchlorohydridotris(triphenylphosphine)ruthenium(II), dihydridotetrakis(triphenylphosphine)ruthenium(II), dihydrobis(acetonitrile)bis(triphenylphosphine)ruthenium(II) and chloro(cyclopentadienyl)bis(triphenylphosphine)ruthenium(II);

"rhodium" such as carbon-supported rhodium, rhodium(III) chloride, chlorotris(triphenylphosphine)rhodium(I), hydridotetrakis(triphenylphoshine)rhodium(I), carbonylhydridotris(triphenylphoshine)rhodium(I), 1,5-cyclooctadiene(diphenylphosphine)rhodium(I) perchlorate, norbornadiene(diphenylphosphine)rhodium(I) perchlorate, diphenylphosphinerhodium(I) perchlorate, 1,1'-bis(diphenylphosphino)ferrocenerhodium(I) perchlorate and 1,3-bis(diisopropylphosphinopropane)rhodium(I) perchlorate;

"palladium" such as carbon-supported palladium, barium sulfate-supported palladium, barium carbonate-supported palladium, calcium carbonate-supported palladium, alumina-supported palladium, palladium(II) chloride, palladium(II) bromide, palladium(II) acetate, trifluoroacetyl palladium(II), bis(acetylacetonato)palladium (II), dichloro(1,5-cyclooctadiene)palladium(II), dichlorobis(benzonitrile)palladium(II), dichlorobis(acetonitrile)palladium(II), dichlorobis(triethylphoshine)palladium(II), dichlorobis(triphenylphosphine)palladium(II), tetrakis(triethylphosphine)palladium and tetrakis(triphenylphosphine)palladium; and "platinum" such as carbon-supported platinum, barium sulfate-supported platinum, barium carbonate-supported platinum, calcium carbonate-supported platinum, alumina-supported platinum, platinum(II) chloride, platinum(II) bromide, platinum(II) acetate, trifluoroacetyl palladium(II), bis(acetylacetonato) platinum (II), dichloro(1,5-cyclooctadiene)platinum(II), dichlorobis(benzonitrile)platinum(II), dichlorobis(acetonitrile)platinum(II), dichlorobis(triethylphoshine)platinum(II), dichlorobis(triphenylphosphine)platinum (II), and tetrakis(trialkylphosphine)platinum such as tetrakis(triethylphosphine)platinum and tetrakis(triphenylphosphine)platinum, and the like.

The transition metal catalyst is preferably carbon-supported ruthenium, ruthenium(III) chloride, ruthenium dioxide, dichlorotris(triphenylphosphine)ruthenium(II), carbon-supported rhodium, rhodium(III) chloride, chlorotris(triphenylphosphine)rhodium(I), carbon-supported palladium, palladium(II) chloride, palladium(II) acetate, dichlorobis(triphenylphosphine)palladium(II) or carbon-supported platinum; more preferably carbon-supported palladium, rhodium(III) chloride or ruthenium(III) chloride; and even more preferably the ruthenium(III) chloride.

The deallylation with ruthenium(III) chloride has not described in any literatures and a novel finding.

The amount of the transition metal catalyst to be used is preferably 0.0001 to 10 times by mole, more preferably 0.001 to 1 time by mole, and more preferably 0.001 to 0.1 time by mole, relative to the mole of the compound (2).

The amount of water to be used is not particularly limited; but is preferably 50 parts by weight or less, and more preferably 20 parts by weight or less, relative to the weight of the compound (2).

When the starting material is hardly dissolved in water, an organic solvent may further be added to assist dissolution of the starting material, to accelerate the reaction.

The organic solvent is not particularly limited, and for example, the solvents exemplified as the reaction solvent in step 1 may be used.

The amount of the organic solvent to be used is not particularly limited; but is preferably 50 parts by weight or less, and more preferably 20 parts by weight or less, relative to the weight of the compound (2), since too large amount of the solvent is disadvantageous to costs and post-treatment.

An acid may further be added for the purposes of increasing the solubility of the starting material in water as well as promoting the hydrolysis of enamine.

Examples of the acid include inorganic acids such as hydrogen fluoride, hydrogen chloride, hydrogen bromide, hydrogen iodide, sulfuric acid, nitric acid, phosphoric acid and boric acid; carboxylic acids such as formic acid, acetic acid, propionic acid, butyric acid, pivalic acid, chloroacetic acid, trichloroacetic acid, trifluoroacetic acid, oxalic acid, L-tartaric acid, D-tartaric acid and mandelic acid; and sulfonic acids such as methanesulfonic acid, trifluoromethanesulfonic acid, benzenesulfonic acid, p-toluenesulfonic acid and camphorsulfonic acid. The acid is preferably hydrogen chloride, hydrogen bromide, sulfuric acid, acetic acid, pivalic acid, oxalic acid, L-tartaric acid, D-tartaric acid, mandelic acid, methanesulfonic acid, p-toluenesulfonic acid or camphorsulfonic acid; more preferably hydrogen chloride or acetic acid; and even more preferably hydrogen chloride. Hydrogen chloride is gaseous and difficult to handle, and thus hydrochloric acid may be used instead.

The amount of the acid to be used is preferably 0.5 to 10 times by mole, and more preferably 0.5 to 3.0 times by mole, relative to the mole of the compound (2).

The reaction speed is low when the reaction temperature in the step is too low, while the yield is decreased due to side reaction when the reaction temperature is too high; therefore, the reaction temperature is preferably 20 to 150° C., and more preferably 50 to 120° C. In the step, an adsorbent such as activated charcoal may be added into the reaction mixture in order to remove a substance adversely affecting the reaction and the inactivated catalyst. The amount of activated charcoal to be used is preferably 0.1 to 10 parts by weight, and more preferably 1 to 3 parts by weight, relative to the part by weight of the transition metal catalyst, although the amount is dependent on the kind of the transition metal catalyst.

In the reaction, the addition method and addition order of the compound (2), the transition metal catalyst, water, the organic solvent, the acid and activated charcoal are not particularly limited.

General treatment for obtaining product from reaction mixture may be carried out as a post-treatment of the reaction. For example, water is added to the reaction mixture after the reaction, or an aqueous solution of base, such as an aqueous solution of sodium hydroxide or an aqueous solution of sodium carbonate, is added for neutralization if necessary; and then, extraction is carried out with a general extraction solvent such as ethyl acetate, diethyl ether, methylene chloride, toluene or hexane. The extract thus obtained is subjected to procedures such as heating under reduced pressure for distilling off the reaction solvent and the extraction solvent, to give the desired substance.

The objective product thus obtained has purity sufficient for use in the subsequent step; but the purity may further be improved by general purification method such as crystallization, fractional distillation and column chromatography in order to further increase the yield in the subsequent step or to further increase the purity of the compound obtained in the subsequent step.

The chemical purity or optical purity of the compound (3) may be increased by forming a salt thereof with an acid and precipitating the salt from the solvent as crystals.

Examples of the acid include the acids exemplified above in formation of the salt of the compound (4) in step 1. The acid is preferably hydrogen chloride, hydrogen bromide, sulfuric acid, acetic acid, pivalic acid, oxalic acid, L-tartaric acid, D-tartaric acid, mandelic acid, methanesulfonic acid, p-toluenesulfonic acid or camphorsulfonic acid, and more preferably the hydrogen chloride.

The amount of the acid to be used is preferably 0.5 to 10 times by mole, and more preferably 0.5 to 3 times by mole, relative to the mole of the compound (3).

The solvent used in crystallization is not particularly limited, and examples thereof can include the solvents exemplified above in crystallization of the salt between the compound (4) and the acid in step 1. The solvent is preferably alcohol solvents such as methanol, ethanol, n-propanol, isopropanol, n-butanol, tert-butanol or ethylene glycol; aromatic hydrocarbon solvents such as benzene or toluene; ketone solvents such as acetone or methyl ethyl ketone; or ester solvents such as ethyl acetate, isopropyl acetate or tert-butyl acetate; and more preferably isopropanol, acetone, ethyl acetate or toluene. The only one solvent may be used, or the mixture of the two or more solvents may be used. When the two or more solvents are used in combination, the mixing ratio is not particularly limited.

The amount of the solvent to be used is preferably not higher than 50 times by weight, and more preferably not higher than 20 times by weight, relative to the weight of the compound (3), since too large amount of the solvent is disadvantageous to costs and post-treatment.

The method for crystallization is not particularly limited, and the processes (a) to (e) described above as the method for crystallization of the compound (4) in step 1 may also be used. The method suitable for the combination of the acid and the solvent is also the same as described for the compound (4). Further, seed crystals may be added in crystallization.

The temperature in the crystallization processes (a) to (e) is not particularly limited, and may be selected appropriately depending on the kind of the salt and the kind of the solvent to be used, and may be preferably decided depending on the desired amount of precipitated crystals and the desired quality of the crystals within lower than the temperature at which the salt of the compound (3) is dissolved in the solvent or the mixed solvent to be used.

The salt of the compound (3) precipitated in the crystallization processes (a) to (e) can be separated and obtained by a procedure such as vacuum filtration, pressure filtration or centrifugation. When the purity of the crystals is lowered due to the remaining mother liquid in the crystals, the quality can be improved by further washing the crystals with an organic solvent if necessary.

Drying under reduced pressure or under vacuum at about 60° C. or less is preferable as a method for drying the crystals, so as to avoid thermal decomposition and melting.

The salt of the compound (3) obtained by the above processes may further be treated with a base such as an alkali metal hydroxide to liberate the compound (3), and an operation such as extraction and concentration may be carried out, to obtain the compound (3) with improved chemical purity or optical purity.

EXAMPLES

Hereinafter, the present invention is described in more detail with reference to the Examples. The present invention is obviously not limited by the Examples. In the Examples, the chemical purity of the respective intermediates, the chemical purity of 2-arylpiperazine derivatives as well as the optical purities thereof were analyzed by HPLC described below. The notation "%" for chemical purity refers to % by weight, and "area %" refers to area percentage.

Analysis Method for Chemical Purity

Column: COSMOSIL 5C18ARII, 250×4.6 mm, manufactured by Nacalai Tesque, Inc.
Mobile phase: $KH_2PO_4$ buffer (pH 4.6)/acetonitrile=50/50 (v/v)
Flow rate: 1.5 ml/min
Detection: UV 210 nm
Column temperature: 40° C.

Analysis Method for Optical Purity: (R)-3-(4-chlorophenyl)-1-(phenylmethyl)hexahydropyrazine In the method, the measurement was carried out after the amino group at 4-position of (R)-3-(4-chlorophenyl)-1-(phenylmethyl)hexahydropyrazine is acetylated for protection.
Column: CHIRALCEL AD-H, 250×4.6 mm, manufactured by Daicel Chemical Industries, Ltd.
Mobile phase: hexane/isopropyl alcohol=95/5 (v/v)
Flow rate: 1.0 ml/min
Detection: UV 210 nm
Column temperature: 30° C.
Retention time: acetyl-protected (R)-3-(4-chlorophenyl)-1-(phenylmethyl)hexahydropyrazine, 18.7 min; acetyl-protected (S)-3-(4-chlorophenyl)-1-(phenylmethyl)hexahydropyrazine, 26.5 min

Example 1

Production of (R)-1-(4-chlorophenyl)-2-[(2-hydroxyethyl)(phenylmethyl)amino]-1-ethanol N-Benzylethanolamine (1.36 g, 1.5 equivalents) was added to (R)-4-chloro-styrene oxide (928 mg, 6.0 mmol), and the mixture was stirred at 70° C. for 3 hours. By cooling to room temperature, 2.56 g of the reaction mixture including the title compound was obtained (yield: 86%, chemical purity: 69.0 area %, N-benzyl ethanolamine: 9.2 area %, 10.4 area % of regioisomer was contaminated). The retention time in the chemical purity analysis method was 3.8 min.

$^1$H-NMR (CDCl$_3$): δ(ppm) 1.65 (br, 2H), 2.04-2.74 (m, 3H), 2.83-2.90 (m, 1H), 3.63-3.70 (m, 3H), 3.86 (d, 1H), 4.62-4.66 (m, 1H), 7.20-7.36 (m, 9H)

Example 2

Production of (R)-1-(4-chlorophenyl)-2-[(2-hydroxyethyl)(phenylmethyl)amino]-1-ethanol hydrochloride To a crude product of (R)-1-(4-chlorophenyl)-2-[(2-hydroxyethyl)(phenylmethyl)amino]-1-ethanol (2.56 g, yield: 86%, chemical purity: 69.0 area %, N-benzyl ethanolamine: 9.2 area %, 10.4 area % of regioisomer was contaminated) produced in Example 1, isopropanol (10 ml) was added for dissolution. To the solution, 28 wt % hydrogen chloride solution in isopropanol (1.55 g, 2.0 equivalents) was added to precipitate crystals. After the mixture was stirred at 25° C. for 1 hour, the crystals were separated by filtration under reduced pressure. The crystals were washed with isopropanol (5 mL) and dried under vacuum, to obtain 1.63 g of the title compound as white crystals (yield: 93%, chemical purity: 97.2 area %, N-benzylethanolamine: 0.9 area %, 0.2 area % of regioisomer was contaminated). The retention time in the chemical purity analysis method was 3.8 min.

$^1$H-NMR (D$_2$O): δ(ppm) 3.37-3.62 (m, 4H), 4.03 (m, 2H), 4.49-4.65 (m, 2H), 5.09 (m, 1H), 7.29-7.48 (m, 4H), 7.55 (m, 5H)

Example 3

Production of (R)-1-(4-chlorophenyl)-2-[(2-hydroxyethyl)(phenylmethyl)amino]-1-ethanol To (R)-1-(4-chlorophenyl)-2-[(2-hydroxyethyl)(phenylmethyl)amino]-1-ethanol hydrochloride (1.63 g, 4.8 mmol, chemical purity: 97 area %) produced in Example 2, distilled water (20 mL), toluene (20 mL) and 30 wt % aqueous solution of sodium hydroxide (1.60 g, 2.0 equivalents) were added. The mixture was stirred. After the organic layer and aqueous layer were separated, the organic layer was washed twice with distilled water (20 mL), and was concentrated and dried under vacuum, to give 1.80 g of the title compound as pale yellow oil (yield: 98%, chemical purity: 97.8 area %). The retention time in the chemical purity analysis method was 3.8 min.

Examples 4 to 7

Production of (R)-1-(4-chlorophenyl)-2-[(2-hydroxyethyl)(phenylmethyl)amino]-1-ethanol The production method in Example 1 was carried out under the following solvent and reaction temperature conditions shown below. The results are shown in Table 1. The reaction time was 20 hours.

TABLE 1

| Example No. | Temperature (° C.) | Solvent | Conversion ratio (%) | Chemical purity (area %) | Regioisomer (area %) |
|---|---|---|---|---|---|
| 4 | 25 | water | 92 | 64.3 | 12.7 |
| 5 | 25 | THF/water = 2.5/1 | 67 | 42.7 | 5.3 |
| 6 | 70 | THF | 89 | 62.4 | 7.3 |
| 7 | 70 | toluene | 99 | 69.1 | 11.8 |

THF: tetrahydrofurane
Conversion ratio: calculated by (area value of product)/(area value of starting material + area value of product) * 100

Example 8

Production of (R)-2-[(2-hydroxyethyl)(phenylmethyl)-amino]-1-phenyl-1-ethanol hydrochloride To (R)-styrene oxide (2.43 g, 20.0 mmol), N-benzyl ethanolamine (3.34 g, 1.05 equivalents) was added. The mixture was stirred at 70° C. for 4 hours and then at 100° C. for 1 hour. The mixture was cooled to room temperature to obtain the reaction mixture of the title compound (chemical purity: 75.8 area %, N-benzyl ethanolamine: 4.0 area %, 16.4 area % of regioisomer was contaminated). The reaction mixture was dissolved by adding isopropanol (35 mL), and then 28 wt % hydrogen chloride solution in isopropanol (2.83 g, 1.1 equivalents) was added dropwise thereto; as a result, crystals were precipitated. After the mixture was stirred at 25° C. for 1 hour, the crystals were separated by filtration under reduced pressure. The crystals were washed with toluene (10 mL) and dried under vacuum, to obtain 4.44 g of the title compound as white crystals (yield: 72%, chemical purity: 97.7 area %, N-methyl ethanolamine: 2.6 area %, 8.9 area % of regioisomer was contaminated). The retention time in the chemical purity analysis method was 2.4 min.

$^1$H-NMR (D$_2$O): δ(ppm) 3.49 (m, 4H), 4.02 (m, 2H), 4.52-4.64 (m, 2H), 5.09 (m, 1H), 7.35 (d, 2H), 7.40 (m, 3H), 7.55 (m, 5H)

Example 9

Production of (R)-1-(4-chlorophenyl)-2-[(2-hydroxyethyl)(methyl)amino]-1-ethanol hydrochloride To (R)-4-chloro-styrene oxide (1.55 g, 10.0 mmol), N-methyl ethanolamine (788 mg, 1.05 equivalents) was added; and the mixture was stirred at 100° C. for 15 hours. The mixture was cooled to room temperature to obtain the reaction mixture of the title compound (chemical purity: 79.8 area %, N-methyl ethanolamine: 0.5 area %, 5.4 area % of regioisomer was contaminated). To the reaction mixture, 28 wt % hydrogen chloride solution in isopropanol (1.55 g, 1.2 equivalents) was added, and ethyl acetate (25 mL) was added dropwise thereto; as a result, crystals were precipitated. After the mixture was stirred at 25° C. for 17 hours, the crystals were separated by filtration under reduced pressure. The crystals were washed with ethyl acetate (10 mL), and dried under vacuum, to obtain 2.26 g of the title compound as white crystals (yield: 78%, chemical purity: 91.5 area %, N-methyl ethanolamine was not detected, 3.6 area % of regioisomer was contaminated). The retention time in the chemical purity analysis method was 1.8 min.

$^1$H-NMR (D$_2$O): δ(ppm) 3.06 (s, 3H), 3.43-3.49 (m, 4H), 3.98-4.00 (t, 2H), 5.22 (m, 1H), 7.42-7.49 (m, 4H)

Example 10

Production of (R)-1-(4-chlorophenyl)-2-[(2-hydroxyethyl)(methyl)amino]-1-ethanol To (R)-1-(4-chlorophenyl)-2-[(2-hydroxyethyl)(methyl)amino]-1-ethanol hydrochloride (2.03 g, chemical purity: 91.5 area %, 7.0 mmol) produced in Example 9, distilled water (10 mL), toluene (10 mL) and 30 wt % aqueous solution of sodium hydroxide (1.11 g, 1.1 equivalents) were added. The mixture was stirred. After the organic layer and aqueous layer were separated, the organic layer was washed twice with distilled water (10 mL), and was concentrated and dried under vacuum, to give 1.47 g of the title compound as pale yellow oil (yield: 91%, chemical purity: 95.3 area %). The retention time in the chemical purity analysis method was 1.8 min.

Example 11

Production of (R)-1-(4-chlorophenyl)-2-[(2-hydroxyethyl)(phenyl)amino]-1-ethanol To (R)-4-chloro-styrene oxide (1.55 g, 10.0 mmol), 2-anilinoethanol (1.44 g, 1.05 equivalents) was added; and the mixture was stirred at 60° C. for 15 hours. The mixture was cooled to room temperature to obtain 3.38 of the reaction mixture of the title compound (chemical purity: 52.1 area %, 2-anilinoethanol: 1.5 area %, 28.4 area % of regioisomer was contaminated). The reaction mixture was purified by column chromatography (gel: silica gel, solvent: ethyl acetate/hexane=1/1), and the obtained fractions were concentrated and dried under vacuum, to obtain 1.68 g of the title compound as pale yellow oil (yield: 49%, chemical purity: 91.7 area %; 2-anilinoethanol was not detected; 4.7 area % of regioisomer was contaminated). The retention time in the chemical purity analysis method was 5.6 min.

$^1$H-NMR (CDCl$_3$): δ(ppm) 2.58 (br, 1H), 3.23-3.31 (m, 1H), 3.36-3.40 (m, 1H), 3.62-3.66 (m, 1H), 3.89-3.94 (m, 2H), 4.09-4.14 (m, 2H), 5.06-5.10 (m, 1H), 6.81 (t, 1H), 6.90 (d, 2H), 7.04 (d, 2H), 7.21-7.25 (m, 4H)

Example 12

Production of (R)-1-(4-chlorophenyl)-2-[(2-hydroxyethyl)amino]-1-ethanol

To (R)-4-chloro-styrene oxide (1.84 g, 11.9 mmol), 2-aminoethanol (2.18 g, 3.0 equivalents) was added. The mixture was stirred at 25° C. for 17 hours, to obtain the reaction mixture of the title compound (chemical purity: 70.9 area %). Ethyl acetate (5 mL) and saturated brine (5 mL) were added to the reaction mixture, and the organic layer and aqueous layer were separated. The obtained organic layer was washed twice with distilled water (5 mL), and was concentrated and dried under vacuum, to obtain 1.47 g of the title compound as viscous white solid. A solution consisting of ethyl acetate (4 mL) and hexane (10 mL) was added thereto under heating at 50° C., and the mixture was stirred for 1 hour and then cooled to 25° C. The resulting crystals were collected by filtration under reduced pressure, then washed with hexane (3 mL) and dried under vacuum, to obtain 993 mg of the title compound as white crystals (yield: 39%; chemical purity: 92.5 area %). The retention time in the chemical purity analysis method was 1.7 min.

$^1$H-NMR (CDCl$_3$): δ(ppm) 2.69-2.84 (m, 4H), 2.98 (br, 2H), 3.68 (t, 2H), 4.70-4.73 (m, 1H), 7.23-7.32 (m, 4H)

Example 13

Production of (R)-1-(4-chlorophenyl)-2-[(2-hydroxyethyl)(2-propenyl)amino]-1-ethanol To (R)-1-(4-chlorophenyl)-2-[(2-hydroxyethyl)amino]-1-ethanol (755 mg, 3.5 mmol) produced in Example 12, dimethylacetamide (5 mL), triethylamine (532 mg, 1.5 equivalents) and allyl bromide (508 mg, 1.2 equivalents) were added. The mixture was stirred at 25° C. for 16 hours. Toluene (5 mL) and distilled water (5 mL) were added to the mixture, and the organic layer and aqueous layer were separated. The organic layer was washed twice with distilled water (5 mL), then concentrated and dried under vacuum, to obtain 817 mg of the title compound as colorless oil (yield: 79%, chemical purity: 92.2 area %). The retention time in the chemical purity analysis method was 2.0 min.

$^1$H-NMR (CDCl$_3$): δ(ppm) 2.54-2.69 (m, 3H), 2.80-2.85 (m, 1H), 2.93-3.34 (m, 2H), 3.64-3.70 (m, 2H), 4.67-4.70 (m, 1H), 5.17-5.22 (m, 2H), 5.80-5.89 (m, 1H), 7.26-7.31 (m, 4H)

Example 14

Production of (R)-1-(4-chlorophenyl)-2-[(2-hydroxyethyl)(tert-butoxycarbonyl)amino]-1-ethanol In ethyl acetate (10 mL), (R)-1-(4-chlorophenyl)-2-[(2-hydroxyethyl)amino]-1-ethanol (1.62 g, 7.5 mmol) produced in Example 12 was dissolved; and then di-tert-butyl bicarbonate (1.80 g, 1.1 equivalents) was added thereto at 5° C. The mixture was stirred for 1 hour. The obtained organic layer was washed twice with distilled water (10 mL), then concentrated and dried under vacuum, to obtain 2.70 g of the title compound as colorless oil (yield: 88%, chemical purity: 91.5 area %). The retention time in the chemical purity analysis method was 4.7 min.

$^1$H-NMR (CDCl$_3$): δ(ppm) 1.49 (s, 9H), 2.96-3.12 (m, 1H), 3.13-3.29 (m, 2H), 3.44-3.98 (m, 5H), 4.94-5.11 (m, 1H), 7.31 (m, 4H)

Example 15

Production of (R)-2-(4-chlorophenyl)-4-(phenylmethyl)-1-(2-propenyl)hexahydropyrazine To (R)-1-(4-chlorophenyl)-2-[(2-hydroxyethyl)(phenylmethyl)amino]-1-ethanol produced (490 mg, 1.6 mmol) produced in Example 3, toluene (1.96 g) and triethylamine (406 mg, 2.5 equivalents) were added. The mixture was cooled to −20° C. Methanesulfonyl chloride (404 mg, 2.2 equivalents) was added dropwise thereto and then allylamine (549 mg, 6.0 equivalents) was added dropwise thereto. After the temperature of the mixture was raised to 25° C., the mixture was stirred for 18 hours; and then, 10 wt % aqueous solution of sodium carbonate (5 mL) was added thereto. After the organic layer and aqueous layer were separated, the aqueous layer was extracted by toluene (5 mL). The organic layers were combined and washed twice distilled water (5 mL). The organic layer thus obtained was concentrated and dried under reduced pressure, to obtain 590 mg of the crude product of the title compound as yellow oil (yield: 68%, chemical purity: 65.6 area %). The retention time in the chemical purity analysis method was 18.3 min.

$^1$H-NMR (CDCl$_3$): δ(ppm) 2.03-2.09 (m, 1H), 2.23-2.37 (m, 2H), 2.47-2.52 (m, 1H), 2.73-2.86 (m, 2H), 3.02 (d, 1H), 3.09-3.14 (m, 1H), 3.30-3.33 (m, 1H), 3.49 (s, 2H), 5.03-5.07 (m, 2H), 5.69-5.79 (m, 1H), 7.22-7.31 (m, 9H)

Example 16

Production of (R)-2-(4-chlorophenyl)-4-(phenylmethyl)-1-(2-propenyl)hexahydropyrazine To (R)-1-(4-chlorophenyl)-2-[(2-hydroxyethyl)(phenylmethyl)amino]-1-ethanol (4.34 g, 14.2 mmol) produced by the method of Example 3, toluene (17.38 g) and triethylamine (5.03 g, 3.5 equivalents) were added. The mixture was cooled to −20° C. Methanesulfonyl chloride (5.21 g, 3.2 equivalents) was added dropwise thereto, then allylamine (4.86 g, 6.0 equivalents) was added dropwise thereto. The mixture was stirred for 1.5 hours. The temperature of the mixture was raised to 25° C., and then the mixture was stirred for 17 hours. To the mixture, 10 wt % aqueous solution of sodium carbonate (35.00 g) was added. After the organic layer and aqueous layer were separated, the aqueous layer was extracted by adding toluene (35.00 g). The organic layers were combined, and washed twice with distilled water (35.00 g). The organic layer thus obtained was concentrated, and dried under reduced pressure, to obtain 4.89 g of the crude product of the title compound as yellow oil (yield: 82%, chemical purity: 89.8 area %). The retention time in the chemical purity analysis method was 18.3 min.

Example 17

Production of (R)-2-(4-chlorophenyl)-4-(phenylmethyl)-1-(2-propenyl)hexahydropyrazine To (R)-1-(4-chlorophenyl)-2-[(2-hydroxyethyl)(phenylmethyl)amino]-1-ethanol (612 mg, 2.0 mmol) produced by the method of Example 3, toluene (2.45 g) and triethylamine (709 mg, 3.5 equivalents) were added. The mixture was cooled to 5° C. Methanesulfonyl chloride (733 mg, 3.2 equivalents) was added dropwise thereto, and then allylamine (685 mg, 6.0 equivalents) was added dropwise thereto. The temperature of the reaction mixture was raised to 25° C., and then the mixture was stirred for 17 hours. To the mixture, 10 wt % aqueous solution of sodium carbonate (3.41 g) was added. After the organic layer and aqueous layer were separated, the aqueous layer was extracted by toluene (3 mL). The organic layers were combined, and washed with distilled water (5 mL). The organic layer thus obtained was concentrated, and dried under reduced pressure, to obtain 522 mg of the crude product of the title compound as yellow oil (yield: 80%, chemical purity: 83.4 area %). The retention time in the chemical purity analysis method was 18.3 min.

Example 18

Production of (R)-2-(4-chlorophenyl)-4-(phenylmethyl)-1-(2-propenyl)hexahydropyrazine dihydrochloride The crude product of (R)-2-(4-chlorophenyl)-4-(phenylmethyl)-1-(2-propenyl)hexahydropyrazine (4.89 g, 11.6 mmol) produced by the method of Example 16 was dissolved by adding isopropanol (30 mL). To the solution, 28 wt % hydrogen chloride solution in isopropanol (3.30 g, 2.2 equivalents) was added to precipitate crystals. The mixture was stirred at 25° C. for 30 minutes, then cooled to 5° C., and further aged for 30 minutes. The crystals were separated by filtration under reduced pressure, washed with ethyl acetate (10 mL), and then dried under vacuum, to obtain 4.55 g of the title compound as white crystals (yield: 96%, chemical purity, 98.3 area %). The retention time in the chemical purity analysis method was 18.3 min.

$^1$H-NMR (D$_2$O): δ(ppm) 3.39-3.47 (m, 2H), 3.53-3.79 (m, 4H), 3.89-3.95 (m, 2H), 4.43-4.55 (m, 3H), 5.40-5.54 (m, 2H), 5.71-5.81 (m, 1H), 7.47-7.58 (m, 9H)

Example 19

Production of (R)-2-phenyl-4-(phenylmethyl)-1-(2-propenyl)hexahydropyrazine dihydrochloride To (R)-2-[(2-hydroxyethyl)(phenylmethyl)amino]-1-phenyl-1-ethanol hydrochloride (4.00 g, 12.7 mmol) produced in Example 8, distilled water (40 mL), toluene (40 mL) and 30 wt % aqueous solution of sodium hydroxide (1.70 g, 1.0 equivalent) were added. The mixture was stirred. After the organic layer and aqueous layer were separated, the organic layer was washed twice with distilled water (20 mL), then concentrated and dried under vacuum, to obtain 3.95 g of a concentrate. Ethyl acetate (13.22 g) and triethylamine (4.50 g, 3.5 equivalents) were added to the concentrate, and the mixture was cooled to 5° C. Methanesulfonyl chloride (4.66 g, 3.2 equivalents) was added dropwise thereto, and then allylamine (4.34 g, 6.0 equivalents) was added dropwise thereto. The mixture was stirred for 1 hour. The temperature of the mixture was raised to 25° C., and then the mixture was stirred for 4 hours. To the mixture, 10 wt % aqueous solution of sodium carbonate (21.54 g) was added. After the organic layer and aqueous layer were separated, the organic layer was washed twice with distilled water (20 mL). The organic layer was concentrated. The obtained concentrate was dissolved by adding ethyl acetate (20 mL). To the solution, 28 wt % hydrogen chloride solution in isopropanol (3.60 g, 2.2 equivalents) was added to precipitate crystals. The mixture was stirred at 25° C. for 1 hour. The crystals were separated by filtration under reduced pressure, washed with isopropanol (50 mL), and dried under vacuum, to obtain 2.96 g of the title compound as white crystals (yield: 71%, chemical purity: 98.4 area %). The retention time in the chemical purity analysis method was 7.9 min.

$^1$H-NMR (D$_2$O): δ(ppm) 3.35-3.79 (m, 6H), 3.97 (t, 2H), 4.46-4.60 (m, 3H), 5.45 (d, 1H), 5.55 (d, 1H), 5.72-5.81 (m, 1H), 7.49-7.60 (m, 10H)

Example 20

Production of (R)-2-(4-chlorophenyl)-4-methyl-1-(2-propenyl)hexahydropyrazine dihydrochloride To (R)-1-(4-chlorophenyl)-2-[(2-hydroxyethyl)(methyl)amino]-1-ethanol (1.47 g, 9.1 mmol) produced in Example 10, toluene (10.02 g) and triethylamine (1.70 g, 3.5 equivalents) were added. The mixture was cooled to −20° C. Methanesulfonyl chloride (1.76 g, 3.2 equivalents) was added dropwise thereto, and then allylamine (1.71 g, 6.0 equivalents) was added dropwise thereto. The mixture was stirred for 1 hour. The temperature of the mixture was raised to 25° C., and then the mixture was stirred for 12 hours. To the mixture, 10 wt % aqueous solution of sodium carbonate (10.02 g) was added. After the organic layer and aqueous layer were separated, the organic layer was washed twice with distilled water (10 mL). The obtained organic layer was concentrated. To the concentrate, 28 wt % hydrogen chloride solution in isopropanol (1.42 g, 2.2 equivalents) and acetone (20 mL) were added to precipitate crystals. The mixture was stirred at 25° C. for 1 hour, then the crystals were separated by filtration under reduced pressure, washed with acetone (5 mL) and dried under vacuum, to obtain 1.05 g of the title compound as pale brown crystals (yield: 60%, chemical purity: 91.7 area %). The retention time in the chemical purity analysis method was 18.5 min.

$^1$H-NMR (D$_2$O): δ(ppm) 3.06 (s, 3H), 3.43-3.49 (m, 2H), 3.53-3.60 (m, 1H), 3.64-3.69 (m, 1H), 3.71-3.77 (m, 1H), 3.90-3.96 (m, 3H), 4.57-4.61 (m, 1H), 5.41-5.73 (m, 2H), 5.73-5.79 (m, 1H), 7.51-7.61 (m, 4H Example 21

Production of (R)-2-(4-chlorophenyl)-4-phenyl-1-(2-propenyl)hexahydropyrazine

To (R)-1-(4-chlorophenyl)-2-[(2-hydroxyethyl)(phenyl)amino]-1-ethanol (1.68 g, 4.94 mmol) produced in Example 11, ethyl acetate (10 mL) and triethylamine (1.75 g, 3.5 equivalents) were added. The mixture was cooled to 5° C. Methanesulfonyl chloride (1.81 g, 3.2 equivalents) was added dropwise thereto, and then allylamine (1.69 g, 6.0 equivalents) was added dropwise thereto. The mixture was stirred at 5° C. for 1 hour and then at 25° C. for 2 hours. The reaction mixture was transferred in an autoclave, and stirred at 50° C. for 18 hours. The mixture was cooled to room temperature, and then 10 wt % aqueous solution of sodium carbonate (8.38 g) was added to the mixture. After the organic layer and aqueous layer were separated, the organic layer was washed twice with distilled water (10 mL). The obtained organic layer was concentrated to give 1.11 g of a concentrate as yellow oil (chemical purity: 30.2 area %). The concentrate was purified by column chromatography (gel: silica gel, solvent: ethyl acetate/hexane=1/9), and the obtained fractions were concentrated and dried under vacuum, to obtain 307 mg of the title compound as colorless oil (yield: 19%, chemical purity: 98.1 area %). The retention time in the chemical purity analysis method was 56.6 min.

$^1$H-NMR (CDCl$_3$): δ(ppm) 2.39-2.46 (m, 1H), 2.51-2.57 (m, 1H), 2.69-2.75 (m, 1H), 2.93-2.99 (m, 1H), 3.15-3.22 (m, 2H), 3.39-3.43 (m, 1H), 3.48-3.52 (m, 1H), 3.61-3.67 (m, 1H), 5.08 (m, 1H), 5.11 (m, 1H), 5.73-5.83 (m, 1H), 6.84 (t, 1H), 6.90 (d, 2H), 7.24 (t, 2H), 7.31-7.37 (q, 4H)

xample 22

Production of (R)-2-(4-chlorophenyl)-1,4-di(2-propenyl)hexahydropyrazine

To (R)-1-(4-chlorophenyl)-2-[(2-hydroxyethyl)(2-propenyl)amino]-1-ethanol (724 mg, 2.5 mmol) produced in Example 13, tetrahydrofuran (2.51 g) and triethylamine (868 mg, 3.5 equivalents) were added. The mixture was cooled to 5° C. Methanesulfonyl chloride (899 mg, 3.2 equivalents) was added dropwise thereto, and then allylamine (839 mg, 6.0 equivalents) was added dropwise thereto. The temperature of the mixture was raised to 25° C., and then the mixture was stirred for 12 hours. To the mixture, 10 wt % aqueous solution of sodium carbonate (4.15 g) was added. After the organic layer and aqueous layer were separated, the aqueous layer was extracted with toluene (5 mL). The organic layers were combined, and washed twice with distilled water (5 mL). The obtained organic layer was concentrated and dried under vacuum, to obtain 709 mg of the title compound as pale yellow oil (yield: 92%, chemical purity: 81.7 area %).

$^1$H-NMR (CDCl$_3$): δ(ppm) 1.99 (t, 1H), 2.21 (m, 1H), 2.33 (m, 1H), 2.47-2.53 (m, 1H), 2.76-2.81 (m, 1H), 2.88-2.92 (m, 1H), 2.98 (t, 2H), 3.03-3.07 (m, 1H), 3.11-3.17 (m, 1H), 3.29-3.33 (m, 1H), 5.04-5.17 (m, 4H), 5.81-5.88 (m, 2H), 7.26-7.32 (q, 4H)

Example 23

Production of (R)-2-(4-chlorophenyl)-1,4-di(2-propenyl)hexahydropyrazine dihydrochloride In toluene (5 mL), (R)-2-(4-Chlorophenyl)-1,4-di(2-propenyl)hexahydropyrazine (613 mg, 2.2 mmol) produced in Example 22 was dissolved. To the solution, 28 wt % hydrogen chloride solution in isopropanol (615 mg, 2.2 equivalents) was added, to precipitate crystals. The mixture was stirred at 25° C. for 1 hour. The crystals were separated by filtration under reduced pressure, washed with toluene (5 mL) and dried under vacuum, to obtain 643 mg of the title compound as white crystals (yield: 93%, chemical purity: 92.7 area %). The retention time in the chemical purity analysis method was 7.4 min.

$^1$H-NMR (D$_2$O): δ(ppm) 3.38-3.52 (m, 3H), 3.59-3.68 (m, 2H), 3.90-3.98 (m, 5H), 4.52-4.56 (m, 1H), 5.43 (d, 1H), 5.53 (d, 1H), 5.61-5.66 (m, 2H), 5.73-5.83 (m, 1H), 5.88-5.98 (m, 1H), 7.50-7.60 (m, 4H)

Example 24

Production of (R)-ethyl-3-(4-chlorophenyl)-4-(2-propenyl)hexahydro-1-pyrazinecarboxylate In distilled water (5 mL), (R)-2-(4-Chlorophenyl)-4-(phenylmethyl)-1-(2-propenyl)hexahydropyrazine dihydrochloride (400 mg, 1.0 mmol) produced in Example 18 was dissolved. To the solution, toluene (5 mL) and 30 wt % aqueous solution of sodium hydroxide (401 mg, 3.0 equivalents) were added. After the organic layer and aqueous layer were separated, the organic layer was washed twice with distilled water (5 mL) and then concentrated. To the concentrate, hexane (5 mL) and ethyl chlorocarbonate (163 mg, 1.5 equivalents) were added. The mixture was stirred at 25° C. for 24 hours. Further, ethyl chlorocarbonate (328 mg, 3.0 equivalents) was added, and the mixture was stirred at 40° C. for 24 hours. After the mixture was cooled to 5° C., the precipitated crystals were collected by filtration under reduced pressure, washed with hexane (2 mL), and dried under vacuum, to obtain 22.5 mg of the title compound as while crystals (yield: 7%, chemical purity: 92.5 area %). Further, the filtrate was concentrated. To the concentrate, toluene (5 mL) was added and the toluene was distilled away. The operation was repeated 3 times. The obtained concentrate was dried under vacuum, to obtain 212 mg of the title compound as while turbid oil (yield: 69%, chemical purity: 95.9 area %). The retention time in the chemical purity analysis method was 22.7 min.

$^1$H-NMR (CDCl$_3$): δ(ppm) 1.27 (t, 3H), 2.88 (m, 1H), 3.25 (m, 1H), 3.62 (m, 2H), 3.83 (m, 2H), 4.05-4.42 (m, 5H), 5.36 (d, 1H), 5.56 (d, 1H), 5.98 (m, 1H), 7.48 (m, 2H), 7.84 (m, 2H)

Example 25

Production of (R)-3-(4-chlorophenyl)-1-(phenylmethyl)hexahydropyrazine dihydrochloride To (R)-2-(4-chlorophenyl)-4-(phenylmethyl)-1-(2-propenyl)hexahydropyrazine (357 mg, 1.1 mmol) produced in Example 15, ethanol (3 mL), distilled water (0.2 mL) and tris(triphenylphosphine) rhodium chloride (30 mg, 0.05 equivalent) were added. The mixture was stirred at 95° C. for 18 hours, and was concentrated. To the concentrate, 1 N hydrochloric acid (5 mL) and toluene (5 mL) were added; and formed insolubles were removed by filtration. After the organic layer and aqueous layer was separated, the obtained aqueous layer (yield: 63%, chemical purity: 77.5 area %, optical purity: 97.7% e.e.) was concentrated. To the concentrate, acetone (10 mL) was added to precipitate crystals. The mixture was stirred at 25° C. for 1 hour, then cooled to 5° C., and further stirred for 1 hour. The crystals were separated by filtration under reduced pressure, then washed with acetone (5 mL), and dried under vacuum, to obtain 134 mg of the title compound as white crystals (yield: 44%, chemical purity: 99.1 area %, optical purity: 99.9% e.e.). The retention time in the chemical purity analysis method was 3.1 min.

$^1$H-NMR (D$_2$O): δ(ppm) 3.28 (t, 1H), 3.38-3.54 (m, 2H), 3.65-3.76 (m, 3H), 4.33 (q, 2H), 4.58 (d, 1H), 7.43 (d, 2H), 7.50 (m, 5H), 7.52 (d, 2H)

TABLE 2

| Example No. | Catalyst | Conversion ratio (%) |
|---|---|---|
| 27 | Palladium chloride | 16 |
| 28 | Palladium acetate | 8 |
| 29 | Bis(triphenylphosphine)palladium chloride | 3 |
| 30 | Ruthenium oxide | 1 |
| 31 | Tris(triphenylphosphine)ruthenium chloride | 7 |
| 32 | Rhodium chloride | 68 |

Conversion ratio: calculated by (area value of product)/(area value of starting material + area value of product) * 100

Examples 33 to 38

The ruthenium chloride in the reaction described in Example 26 was changed to the catalysts shown in Table 3 below, and the reaction was carried out.

TABLE 3

| Example No. | Catalyst | Catalyst amount to starting material (wt %) | Reaction time (hours) | Conversion ratio (%) |
|---|---|---|---|---|
| 33 | 5% Palladium/carbon | 10 | 15 | 5 |
| 34 | 10% Palladium/carbon | 10 | 15 | 31 |
| 35 |  | 60 | 72 | 96 |
| 36 | 5% Platinum/carbon | 10 | 15 | 6 |
| 37 | 5% Ruthenium/carbon | 10 | 15 | 2 |
| 38 | 5% Rhodium/carbon | 10 | 15 | 1 |

Conversion ratio: calculated by (area value of product)/(area value of starting material + area value of product) * 100

Example 26

Production of (R)-3-(4-chlorophenyl)-1-(phenylmethyl)hexahydropyrazine dihydrochloride Mixed were (R)-2-(4-Chlorophenyl)-4-(phenylmethyl)-1-(2-propenyl)hexahydropyrazine dihydrochloride (104 mg, 0.25 mmol) produced in Example 18 and ruthenium chloride (3 mg, 0.04 mmol). The mixture was stirred at 100° C. for 24 hours. To the mixture, 30 wt % aqueous solution of sodium hydroxide (85 mg, 2.5 equivalents) and toluene (2 mL) were added. The formed insolubles were separated by filtration, and washed with distilled water (2 mL) and toluene (2 mL). After the organic layer and aqueous layer of the filtrate were separated, the organic layer was washed twice with distilled water (4 mL). The obtained organic layer was concentrated and dried under vacuum, to obtain 68 mg of the crude product of the title compound as pale brown oil (yield: 87%, chemical purity: 93.5 area %, optical purity: 98.1% e.e.). The retention time in the chemical purity analysis method was 3.1 min.

Examples 27 to 32

The ruthenium chloride in the reaction described in Example 26 was changed to the catalysts (0.04 equivalent) shown in Table 2 below, and the reaction was carried out for 15 hours.

Example 39

Production of (R)-3-phenyl-1-(phenylmethyl)-hexahydropyrazine

In distilled water (3 mL), (R)-2-Phenyl-4-(phenylmethyl)-1-(2-propenyl)hexahydropyrazine dihydrochloride (328 mg, 1.0 mmol) produced in Example 19 was dissolved. To the solution, ruthenium chloride (5 mg, 0.02 equivalent) and activated charcoal (6 mg) were added. The mixture was stirred at 100° C. for 24 hours. To the mixture, 30 wt % aqueous solution of sodium hydroxide (295 mg, 2.2 equivalents) and toluene (3 mL) were added. The formed insolubles were separated by filtration, and washed with toluene (3 mL). After the organic layer and aqueous layer of the filtrate were separated, the organic layer was washed twice with distilled water (6 mL). The organic layer was concentrated and dried under vacuum, to obtain 227 mg of the title compound as pale brown oil (yield: 91%, chemical purity: 94.8 area %). The retention time in the chemical purity analysis method was 2.4 min.

$^1$H-NMR (CDCl$_3$): δ(ppm) 1.74 (br, 1H), 2.06 (t, 1H), 2.15-2.21 (m, 1H), 2.82-2.92 (m, 2H), 3.04-3.07 (m, 2H), 3.54 (s, 2H), 3.86-3.90 (m, 1H), 7.22-7.37 (m, 10H)

Example 40

Production of
(R)-3-(4-chlorophenyl)-1-methyl-hexahydropyrazine

In distilled water (9 mL), (R)-2-(4-Chlorophenyl)-4-methyl-1-(2-propenyl)hexahydropyrazine dihydrochloride (1.06 g, 3.0 mmol) produced in Example 20 was dissolved. To the solution, ruthenium chloride (28 mg, 0.04 equivalent) was added. The mixture was stirred at 100° C. for 12 hours. After toluene (9 mL) was added thereto, formed insolubles were removed by filtration, and washed with toluene (9 mL) and distilled water (9 mL). To the filtrate, 30 wt % aqueous solution of sodium hydroxide (918 mg, 2.5 equivalents) was added. After the organic layer and aqueous layer were separated, the organic layer was washed twice with distilled water (9 mL), concentrated and dried under vacuum, to obtain 448 mg of the title compound as pale brown oil (yield: 65%, chemical purity: 88.4 area %). The retention time in the chemical purity analysis method was 2.2 min.
$^1$H-NMR (CDCl$_3$): δ(ppm) 1.71 (br, 1H), 1.91-1.97 (m, 1H), 2.05-2.08 (m, 1H), 2.31 (s, 3H), 2.80-2.84 (m, 2H), 3.02-3.07 (m, 2H), 3.83-3.86 (m, 1H), 7.26-7.34 (m, 4H)

Example 41

Production of
(R)-3-(4-chlorophenyl)-1-phenyl-hexahydropyrazine

To (R)-2-(4-chlorophenyl)-4-phenyl-1-(2-propenyl)hexahydropyrazine dihydrochloride (285 mg, 0.87 mmol) produced in Example 21, distilled water (2 mL), conc. hydrochloric acid (181 mg, 2.0 equivalents), ruthenium chloride (9 mg, 0.04 equivalent) and activated charcoal (9 mg) were added. The mixture was stirred at 100° C. for 18 hours. Toluene (4 mL) and 30 wt % aqueous solution of sodium hydroxide (258 mg, 2.2 equivalents) were added thereto. The formed insolubles were removed by filtration, and washed with toluene (2 mL). After the organic layer and aqueous layer of the filtrate were separated, the organic layer was washed twice with distilled water (6 mL). The organic layer was concentrated and dried under vacuum, to obtain 89 mg of the title compound as brown oil (yield: 29%, chemical purity: 83.8 area %). The retention time in the chemical purity analysis method was 3.7 min.
$^1$H-NMR (CDCl$_3$): δ(ppm) 1.72 (br, 1H), 2.63-2.69 (m, 1H), 2.86-2.91 (m, 1H), 3.12-3.25 (m, 2H), 3.60 (t, 2H), 3.94-3.97 (m, 1H), 6.86 (t, 1H), 6.93 (d, 2H), 7.25 (t, 2H), 7.31-7.40 (d, 4H)

Example 42

Production of
(R)-2-(4-chlorophenyl)hexahydropyrazine

In distilled water (2 mL), (R)-2-(4-Chlorophenyl)-1,4-di(2-propenyl)hexahydropyrazine dihydrochloride (288 mg, 0.75 mmol) produced in Example 23 was dissolved. Ruthenium chloride (15 mg, 0.08 equivalent) was added thereto, and the mixture was stirred at 100° C. for 68 hours. The mixture was cooled, and then toluene (5 mL) was added thereto. The organic layer was discarded; and toluene (5 mL), distilled water (4 mL) and 30 wt % aqueous solution of sodium hydroxide (250 mg, 2.5 equivalents) were added to the aqueous layer. The formed insolubles were removed by filtration, the aqueous layer was removed, and the organic layer was washed with distilled water (2 mL). The organic layer was concentrated and dried under vacuum, to obtain 82 mg of pale brown oil (yield: 39%). Further, hexane (2 mL) was added thereto to precipitate crystals. After the mixture was stirred at 25° C. for 1 hour, the crystals were separated by filtration under reduced pressure, washed with hexane (1 mL), and dried under vacuum, to obtain 35.6 mg of the title compound as pale violet crystals (yield: 43%, chemical purity: 83.6 area %). The retention time in the chemical purity analysis method was 1.8 min.
$^1$H-NMR (CDCl$_3$): δ(ppm) 1.68 (br, 2H), 2.62-2.68 (m, 1H), 2.85-3.00 (m, 4H), 3.08-3.11 (m, 1H), 3.71-3.74 (m, 1H), 7.26-7.33 (d, 4H)

Example 43

Production of (R)-ethyl-3-(4-chlorophenyl)-hexahydro-1-pyrazinecarboxylate

To (R)-ethyl-3-(4-chlorophenyl)-4-(2-propenyl)hexahydro-1-pyrazinecarboxylate (212 mg, 0.69 mmol) produced in Example 24, distilled water (2 mL), conc. hydrochloric acid (71 mg, 1.0 equivalent) and ruthenium chloride (7 mg, 0.04 equivalent) were added. The mixture was stirred at 100° C. for 93 hours. After toluene (2 mL) was added thereto, the formed insolubles were separated by filtration and washed with toluene (2 mL) and distilled water (2 mL). To the filtrate, 30 wt % aqueous solution sodium hydroxide (110 mg, 1.2 equivalents) was added. The organic layer and aqueous layer were separated, and the organic layer was washed twice with distilled water (4 mL). The obtained organic layer was concentrated and dried under vacuum, to obtain 72 mg of the title compound as pale brown oil (yield: 38%, chemical purity: 92.6 area %). The retention time in the chemical purity analysis method was 2.9 min.
$^1$H-NMR (CDCl$_3$): δ(ppm) 1.27 (t, 3H), 1.63 (br, 1H), 2.71 (m, 1H), 2.85-3.04 (m, 2H), 3.08 (d, 1H), 3.69 (d, 1H), 3.95-4.25 (m, 4H), 7.29-7.36 (m, 4H)

Example 44

Production of (R)-3-(4-chlorophenyl)-1-(phenylmethyl)hexahydropyrazine

To (R)-1-(4-chlorophenyl)-2-[(2-hydroxyethyl)(phenylmethyl)amino]-1-ethanol (490 mg, 1.6 mmol) produced by the method of Example 3, toluene (1.96 g) and triethylamine (405 mg, 2.5 equivalents) were added. The mixture was cooled to 5° C. Methanesulfonyl chloride (403 mg, 2.2 equivalents) was added dropwise thereto, and then 5 N ammonia solution in methanol (4 mL 12.5 equivalents) was added dropwise thereto. The temperature of the mixture was raised to 25° C., and then the mixture was stirred for 17 hours. After the mixture was concentrated, distilled water (5 mL), toluene (5 mL) and further 30 wt % aqueous solution of sodium hydroxide (534 mg, 2.5 equivalents) were added for extraction. After the organic layer and aqueous layer were separated, the organic layer was washed twice with distilled water (5 mL), concentrated and dried under vacuum, to obtain 483 mg of the crude product of the title compound was as colorless oil (yield: 27%, chemical purity: 61.3 area %, optical purity: 98.7% e.e.). The retention time in the chemical purity analysis method was 3.1 min.

Example 45

Production of (R)-3-(4-chlorophenyl)-1-(phenylmethyl)hexahydropyrazine dihydrochloride In isopropanol (2 mL), (R)-3-(4-Chlorophenyl)-1-(phenylmethyl)hexahydropyrazine (197 mg, 0.17 mmol, optical purity: 98.7% e.e.) produced in Example 44 was dissolved; and conc. hydrochloric acid (106 mg, 6.0 equivalents) was added thereto. The mixture was stirred. The solution was concentrated, acetone (2.5 mL) was added thereto, and the temperature of the mixture was raised to 50° C. to obtain a homogenous solution. The solution was cooled to 25° C., and acetone (5 mL) and seed crystals were added thereto, to precipitate crystals. The mixture was concentrated to the original liquid volume, and stirred at 25° C. for 1 hour and further at 5° C. for 1 hour. The crystals were collected by filtration under reduced pressure, and then washed with acetone (1.5 mL) and dried under vacuum, to obtain 11.1 mg of the title compound as white crystals (yield: 17%, chemical purity: 98.0 area %, optical purity: 99.8% e.e.). The retention time in the chemical purity analysis method was 3.1 min.

Example 46

Production of (R)-2-(4-chlorophenyl)-1-methyl-4-(phenylmethyl)hexahydropyrazine dihydrochloride To (R)-1-(4-chlorophenyl)-2-[(2-hydroxyethyl)(phenylmethyl)amino]-1-ethanol (610 mg, 2.0 mmol) produced by the method of Example 3, toluene (2.44 g) and triethylamine (708 mg, 3.5 equivalents) were added. The mixture was cooled to −20° C. Methanesulfonyl chloride (734 mg, 3.2 equivalents) was added dropwise thereto, and then 40 wt % aqueous solution of methylamine (932 mg, 6.0 equivalents) was added dropwise thereto. The mixture was stirred at −20° C. for 1 hour, then the temperature of the reaction mixture was raised to 25° C., and the mixture was stirred for 16 hours. To the reaction mixture, 10 wt % aqueous solution of sodium carbonate (3.39 g, 1.6 equivalents) was added. After the organic layer and aqueous layer were separated, the organic layer was washed twice with distilled water (3 mL) and concentrated. Isopropanol (8 mL) was added to the concentrate, and then the mixture was concentrated again. The obtained concentrate was dissolved in isopropanol (5 mL), and 28 wt % hydrogen chloride solution in isopropanol (568 mg, 2.2 equivalents) was added to the solution, to precipitate crystals. The mixture was stirred at 25° C. for 2 hours; and then the crystals were separated by filtration under reduced pressure, washed with isopropanol (2 mL) and dried under vacuum, to obtain 521 mg of the title compound as white crystals (yield: 66%, chemical purity: 98.6 area %). The retention time in the chemical purity analysis method was 7.7 min.

$^1$H-NMR (D$_2$O): δ(ppm) 2.71 (s, 3H), 3.55-3.67 (m, 2H), 3.74-3.80 (m, 2H), 3.90-3.97 (m, 2H), 4.46-4.57 (m, 3H), 7.47-7.59 (m, 9H)

Example 47

Production of (R)-2-(4-chlorophenyl)-1-(1,1-dimethylethyl)-4-(phenylmethyl)hexahydropyrazine dihydrochloride To (R)-1-(4-chlorophenyl)-2-[(2-hydroxyethyl)(phenylmethyl)amino]-1-ethanol (610 mg, 2.0 mmol) produced by the method of Example 3, toluene (2.44 g) and triethylamine (708 mg, 3.5 equivalents) were added. The mixture was cooled to 5° C. Methanesulfonyl chloride (734 mg, 3.2 equivalents) was added dropwise thereto and then tert-butylamine (879 mg, 6.0 equivalents) was added dropwise thereto. The mixture was stirred at 5° C. for 1 hour, and then the temperature of the mixture was raised to 25° C. and the mixture was stirred for 16 hours. To the reaction mixture, 10 wt % aqueous solution of sodium carbonate (3.39 g, 1.6 equivalents) was added. After the organic layer and aqueous layer were separated, the organic layer was washed twice with distilled water (3 mL) and concentrated. Isopropanol (8 mL) was added to the concentrate, and the mixture was concentrated again. The obtained concentrate was dissolved in isopropanol (5 mL), and 28 wt % hydrogen chloride solution in isopropanol (570 mg, 2.2 equivalents) was added to the solution, to precipitate crystals. The mixture was stirred at 25° C. for 3 hours, and then the crystals were separated by filtration under reduced pressure, washed with isopropanol (2 mL) and dried under vacuum, to obtain 192 mg of the title compound as white crystals (yield: 18%, chemical purity: 98.0 area %). The retention time in the chemical purity analysis method was 6.2 min.

$^1$H-NMR (D$_2$O): δ(ppm) 1.20 (s, 9H), 3.37-3.57 (m, 4H), 3.79 (m, 1H), 3.98-4.04 (m, 1H), 4.23-4.35 (m, 2H), 4.70-4.74 (m, 1H), 7.47 (bs, 5H), 7.55 (bs, 4H)

The invention claimed is:
1. A method for producing an optically active 2-arylpiperazine derivative or salt thereof, comprising steps of:
treating an optically active substituted aminodiol derivative represented by the following formula (4):

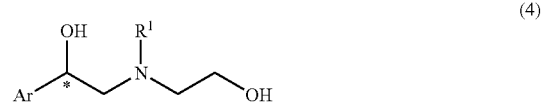

wherein, Ar represents an optionally substituted aryl group having 6 to 20 carbon atoms, or an optionally substituted heteroaryl group having 3 to 20 carbon atoms; R$^1$ represents an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; * indicates an asymmetric carbon atom, with a sulfonating agent in the presence of a base;
and then reacting with an amine compound represented by the following formula (5):

wherein, R$^2$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms;
wherein, the optically active 2-arylpiperazine derivative is represented by the following formula (1):

wherein, Ar, R$^1$, R$^2$, * mean the same as the above, and the configuration of the optically active 2-arylpiperazine derivative represented by formula (1) is S when the configuration of the optically active substituted aminodiol derivative represented by formula (4) is S, or the configuration of the optically active 2-arylpiperazine derivative represented by formula (1) is R when the configuration of the optically active substituted aminodiol derivative represented by formula (4) is R.

2. The production method according to claim 1, wherein the base is triethylamine and the sulfonating agent is methanesulfonyl chloride.

3. The production method according to claim 1, wherein the optically active substituted aminodiol derivative represented by the formula (4) is produced by reacting an optically active styrene oxide derivative represented by the following formula (6):

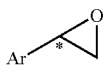
(6)

wherein, Ar, * mean the same as the above,
with an aminoethanol derivative represented by the following formula (7):

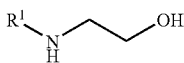
(7)

wherein, R¹ means the same as the above.

4. The production method according to claim 3, wherein
a salt is formed from the optically active substituted aminodiol derivative represented by formula (4) and an acid, and is crystallized from a solvent to be precipitated as a crystal; and
a regioisomer (8):

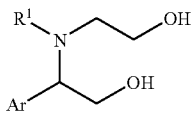
(8)

wherein, Ar, R¹ mean the same as the above,
yielded as a by-product at the reaction of the optically active styrene oxide derivative represented by formula (6) and the aminoethanol derivative represented by formula (7) is removed into a mother liquid.

5. The production method according to claim 1, wherein the optically active substituted aminodiol derivative represented by the formula (4) is produced by reacting an optically active styrene oxide derivative represented by the following formula (6):

(6)

wherein, Ar, * mean the same as the above,
with an aminoethanol represented by the following formula (7'):

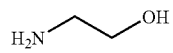
(7')

to produce an optically active aminodiol derivative represented by the following formula (4'):

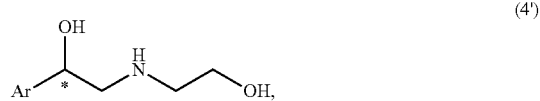
(4')

wherein, Ar, * mean the same as the above,
and then introducing a substituent at the amino group.

6. The production method according to claim 1, wherein Ar is a phenyl group or a 4-chlorophenyl group; R¹ is a methyl group, an allyl group, a benzyl group or a phenyl group; R² is a hydrogen atom, a methyl group, a tert-butyl group or an allyl group.

7. The production method according to claim 1, wherein R² is an allyl group.

8. The production method according to claim 7, wherein the optically active 2-arylpiperazine derivative represented by the formula (1) or salt thereof is treated with water in the presence of a transition metal catalyst to produce an optically active 1-unsubstituted-2-arylpiperazine derivative represented by the following formula:

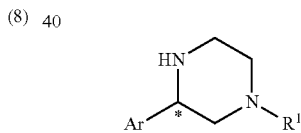

wherein, Ar, R¹, * mean the same as the above.

9. The production method according to claim 8, wherein the transition metal catalyst is Ruthenium (III) chloride.

10. The production method according to claim 7, wherein Ar is a phenyl group or a 4-chlorophenyl group; R¹ is a methyl group, an allyl group, a benzyl group or a phenyl group.

11. The production method according to claim 1, wherein the reaction temperature for the step of sulfonylation is maintained in a range of −40° C. to 5° C.

* * * * *